US009102726B2

(12) United States Patent
Steinkasserer et al.

(10) Patent No.: US 9,102,726 B2
(45) Date of Patent: Aug. 11, 2015

(54) NUCLEIC ACID OF RECOMBINATION EXPRESSION VECTOR ENCODING SOLUBLE FORMS OF CD83, HOST CELLS TRANSFORMED/TRANSFECTED THEREWITH AND PHARMACEUTICAL COMPOSITIONS CONTAINING SAME

(75) Inventors: Alexander Steinkasserer, Bruckenhof (DE); Matthias Lechmann, Bamberg (DE); Elisabeth Zinser, Buckenhof (DE)

(73) Assignee: ARGOS THERAPEUTICS, INC., Durham, NC (US)

( * ) Notice: Subject to any disclaimer, the term of this patent is extended or adjusted under 35 U.S.C. 154(b) by 1209 days.

(21) Appl. No.: 10/382,397

(22) Filed: Mar. 6, 2003

(65) Prior Publication Data
US 2004/0110673 A1 Jun. 10, 2004

Related U.S. Application Data

(63) Continuation-in-part of application No. 10/309,611, filed on Dec. 4, 2002, now Pat. No. 7,169,898.

(51) Int. Cl.
*C07K 16/28* (2006.01)
*C07K 14/705* (2006.01)
*A61K 48/00* (2006.01)
*A61K 38/00* (2006.01)

(52) U.S. Cl.
CPC ....... *C07K 16/2803* (2013.01); *C07K 14/70503* (2013.01); *A61K 38/00* (2013.01); *A61K 48/00* (2013.01); *G01N 2333/70503* (2013.01)

(58) Field of Classification Search
None
See application file for complete search history.

(56) References Cited

U.S. PATENT DOCUMENTS

| | | | |
|---|---|---|---|
| 5,316,920 A | 5/1994 | Tedder | |
| 5,710,262 A * | 1/1998 | Tedder et al. | 536/22.1 |
| 5,766,570 A | 6/1998 | Tedder et al. | |
| 6,068,984 A | 5/2000 | Tedder et al. | |
| 6,197,930 B1 * | 3/2001 | Sheppard et al. | 530/350 |
| 7,169,898 B2 | 1/2007 | Steinkasserer et al. | |
| 7,893,200 B2 | 2/2011 | Steinkasserer et al. | |
| 8,124,099 B2 | 2/2012 | Steinkasserer et al. | |
| 8,759,505 B2 | 6/2014 | Steinkasserer et al. | |
| 2003/0219436 A1 | 11/2003 | Ledbetter et al. | |
| 2004/0185040 A1 | 9/2004 | Garcia-Martinez et al. | |
| 2005/0032725 A1 | 2/2005 | Rao et al. | |
| 2011/0182903 A1 | 7/2011 | Brand et al. | |
| 2014/0010821 A1 | 1/2014 | Nicolette et al. | |

FOREIGN PATENT DOCUMENTS

| | | |
|---|---|---|
| EP | 0 636 176 | 4/1993 |
| EP | 0636176 | 10/1993 |
| EP | 0 636 176 | 10/1999 |
| EP | 1422241 A1 | 5/2004 |
| EP | 1562985 A2 | 6/2004 |
| WO | 96 32965 A1 | 10/1996 |
| WO | 97 29781 | 8/1997 |
| WO | WO 97/29781 | 8/1997 |
| WO | 98 52606 A1 | 11/1998 |
| WO | 00 67796 A1 | 11/2000 |
| WO | WO 02/49625 | 6/2002 |
| WO | WO 03/045318 | 6/2003 |
| WO | WO 03/049625 | 6/2003 |
| WO | 2004 016284 | 1/2004 |
| WO | 2004 0046182 | 6/2004 |
| WO | 2008 024242 A2 | 2/2008 |
| WO | 2009 142759 | 11/2009 |

OTHER PUBLICATIONS

Burgess, W.H., et al. J. Cell Biol. 1990;111:2129-2138.*
Kumar, V., et al. Proc. Nat'l. Acad. Sci., USA. 1990;87:1337-1341.*
Mei et al., 2006, Am J Physiol Cell Physiol. vol. 291: C1022-C1028.*
Lechmann, Matthias, et al; "The extracellular Domain of CD83 Inhibits Dendritic Cell-mediated T Cell Stimulation and Binds to a Ligand on Dendritic Cells"; J. Exp. Med. © The Rockefeller University Press; vol. 194, No. 12, Dec. 17, 2001; pp. 1813-1821.
Lechmann, Mettthais, et al; "CD83 on Dendritic Cells: More Than Just a Marker for Maturation"; Research Update Trends in Immunology, vol. 23, No. 6, Jun. 2002; pp. 273-275.
Lechmann, Matthias, et al; "Overexpression, Purification, and Biochemical Characterization of the Extracellular Human CD83 Dopmain and Generation of Monoclonal Antibodies"; Protein Expression and purification 24, 445-452 (2002).
Lechmann et al., "Role of CD83 in the Immunomodulation of Dendritic Cells", International Archives of Allergy and Immunology, vol. 129, No. 2: 113-118 (Oct. 2002).
Smith et al., "Single-step purification of polypeptides expressed in *Escherichia coli* as fusions with glutathione s-trasferase", Gene, Elsevier Biomedical Press, Amsterdam, NL., vol. 67, No. 1: 31-40. (1988).
N. Scholler et al., J. Immunol., 166: 3865-3872 (2001).
N. Scholler et al., J. Immunol., 168: 2599-2602 (2002).
Cramer, et al, "Activation-induced expression of murine CD83 on T cells and identification of a specific CD83 ligand on murine B cells"; International Immunology, vol. 12, No. 9, pp. 1347-1351.

(Continued)

Primary Examiner — Gerald R Ewoldt
(74) Attorney, Agent, or Firm — Norris McLaughlin & Marcus, P.A.

(57) ABSTRACT

The present invention provides methods of using soluble forms of CD83 and nucleic acids encoding them for the treatment or prevention of diseases caused by the dysfunction or undesired function of a cellular immune response involving T cells. The invention moreover provides soluble CD83 proteins, specifically suited for said purpose, nucleic acids and vectors encoding said CD83 proteins, cells transformed/transfected with the nucleic acids or vectors, methods for producing said CD83 proteins, pharmaceutical compositions containing said CD83 proteins, nucleic acids or vectors, and antibodies against said soluble CD83 proteins and assay methods and kits comprising said antibodies.

7 Claims, 9 Drawing Sheets

(56) References Cited

OTHER PUBLICATIONS

Sittinger et al., Biomaterials, 17: 237-242 (1996).
Kreis et al., Transplant, 69: 1252-1260 (2000).
Neumann et al., J. Amer. Soc. Nephrol., 14: 721-727 (2003).
Wekerle, Ann. Rheum. Dis., 67: (Supp. III): iii56-iii60 (2008).
Prazma et al., Immunol. Lett., 115: 1-8 (2008).
Pashine et al., Immunol. Lett., 115: 9-15 (2008).
Bolton, Inflammopharmacology, 15: 183-187 (2007).
Breloer, Immunol. Lett., 115: 16-17 (2008).
Chou, Immunol. Lett., 115: 20 (2008).
Furlan et al., Method Molecular Biol., 549: 157-173 (2009).
Coisne et al., J. Immunol., 182: 5909-5913 (2009).
Zinser et al., Immunol. Lett., 115: 8-9 (2008).
Nishi, et al; "Expression of a synthetic gene for initiation factor 4E-binding protein 1 in *Escherichia coli* and its interaction with eIF-4E and eIF-4E x m7GTP complex"; J. Biochem, 1990, 123 (1).
Hock et al; "A soluble form of CD83 is released from activated dendritic cells and B lymphocytes, and is detectable in normal human sera"; International Immunology, vol. 13, No. 7, pp. 959-967, 2001.
Breloer (2007) Eur. J. Immunol. 37: 634-638, "CD83 is a regulator of murine B cell function in vivo".
Penna et al. (2001) J. Immunol. 167: 1862-66, "Cutting edge: Selective usage of chemokine receptors by plasmacytoid dendritic cells".
Zinser et al. (2004) J. Exp. Med. 200: 345-351 (entitled, "Prevention and treatment of experimental autoimmune encephalomyelitis by soluble CD83").
Zinser et al. (2006) Immunobiology 211: 449-453, "Determination of the inhibitory activity and biological half-life of soluble CD83: comparison of wild type and mutant isoforms".
Lechmann, Matthias et al; "CD83 is a dimer: comparative analysis of monomeric and dimeric isoforms"; Biochemical and biophysical Research Communications 329 (2005) pp. 132-139.
Bessmertney, et al; "Tacrolimus (FK-506) and mycophenolate mofetil (MMF) GVHD prophylaxis in allogeneic SCT (ALLOSCT) recipients: altered MMF pharmacokinetics (PK) associated with AGVHD"; Biol. Blood & Marrow Transplantation, 2003 p. 93, A94.
Wang et al., "Targeting a novel immunomodulatory protein by soluble CD83 promotes tolerance induction in a mouse cardiac transplantation model," Am. J. Transplant., 2007, p. 579, Abstract #1679, Suppl. S2.
Mor et al., "Identification of aldolase as a target antigen in Alzheimer's disease," J. Immunol., 2005, pp. 3439-3445, vol. 175.
Kobashigawa et al., "Tacrolimus with mycophenolate mofetil (MMF) or sirolimus vs. cyclosporine with MMR in cardiac transplant patients: 1-year report," Am. J. Transplant., 2006, pp. 1377-86, vol. 16.
Kahan et al., "New immunosuppressive drugs: needs in and applications to pediatric transplantation," Eur. J. Pediatr., 1992, pp. S9-S12, vol. 15.
Chevalier et al., "The split personality of regulatory T cells in HIV infection," Blood, 2013, pp. 29-37, vol. 121.
Thangudu et al., "Analycys: a database for conservation and confirmation of disulphide bonds in homologous protein domains" 2007, *Proteins*, vol. 67: 255-261.
National Institutes of Health, The Autoimmune Diseases Coordinating Committee "Progress in Autoimmune Diseases Research", Mar. 2005, pp. 1-126.

\* cited by examiner

```
                              Thrombin cleavage
                                    site         SmaI
                                     |         ------
pGEX2T... CCTCCAAAATCGGATCTGGTTCCGCGTGGATCCCCGGGAACGCCGGAGGT
             P  P  K  S  D  L  V  P  R  G  S  P  G  T  P  E  V GAAGGTGGCTTGCTCCGAAGATGTGGACTTGCCCTGCACCGCCCCCTGGGATCCGCAGGT
  K  V  A  C  S  E  D  V  D  L  P  C  T  A  P  W  D  P  Q  V TCCCTACACGGTCTCCTGGGTCAAGTTATTGGAGGGTGGTGAAGAGAGGATGGAGACACC
  P  Y  T  V  S  W  V  K  L  L  E  G  G  E  E  R  M  E  T  P CCAGGAAGACCACCTCAGGGGACAGCACTATCATCAGAAGGGGCAAAATGGTTCTTTCGA
  Q  E  D  H  L  R  G  Q  H  Y  H  Q  K  G  Q  N  G  S  F  D CGCCCCCAATGAAAGGCCCTATTCCCTGAAGATCCGAAACACTACCAGCTGCAACTCGGG
  A  P  N  E  R  P  Y  S  L  K  I  R  N  T  T  S  C  N  S  G GACATACAGGTGCACTCTGCAGGACCCGGATGGGCAGAGAAACCTAAGTGGCAAGGTGAT
  T  Y  R  C  T  L  Q  D  P  D  G  Q  R  N  L  S  G  K  V  I CTTGAGAGTGACAGGATGCCCTGCACAGCGTAAAGAAGAGACTTTTAAGAAATACAGAGC
  L  R  V  T  G  C  P  A  Q  R  K  E  E  T  F  K  K  Y  R  A GGAGATTTGAGAATTCATCGTGACT ...pGEX2T
  E  I  -  ------
            EcoRI
```

Fig.1

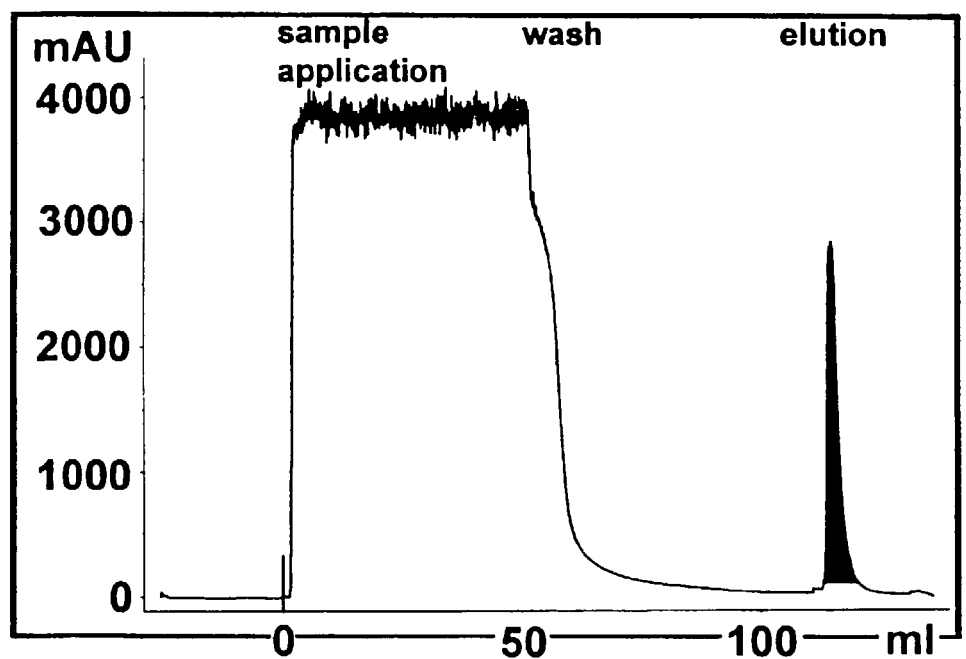
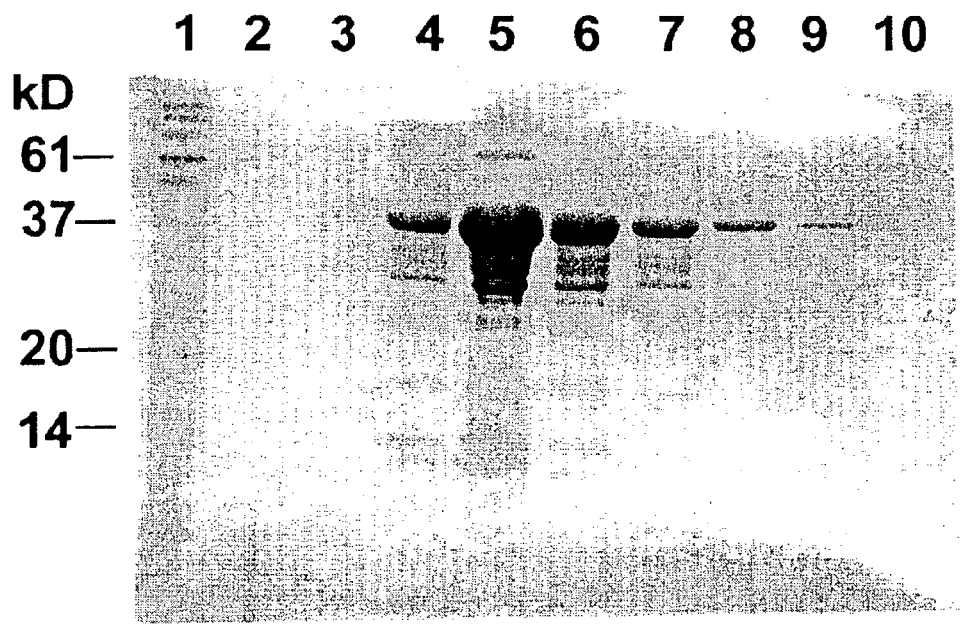
Fig.2 A

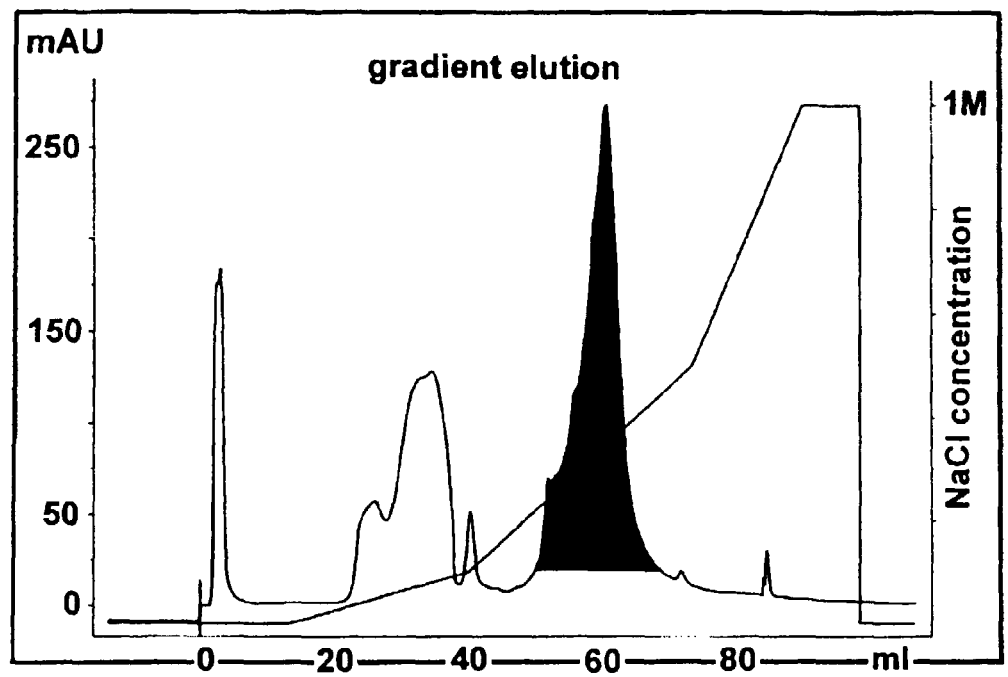
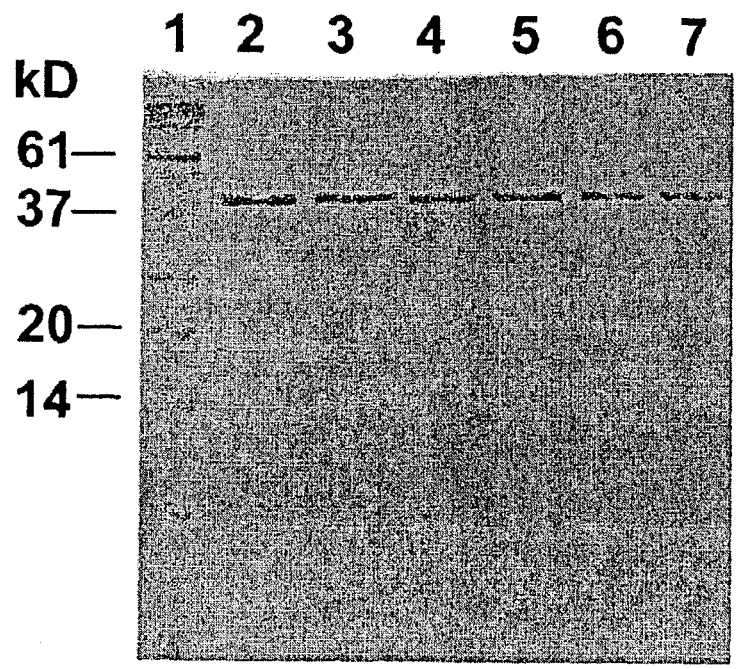
Fig. 2 B

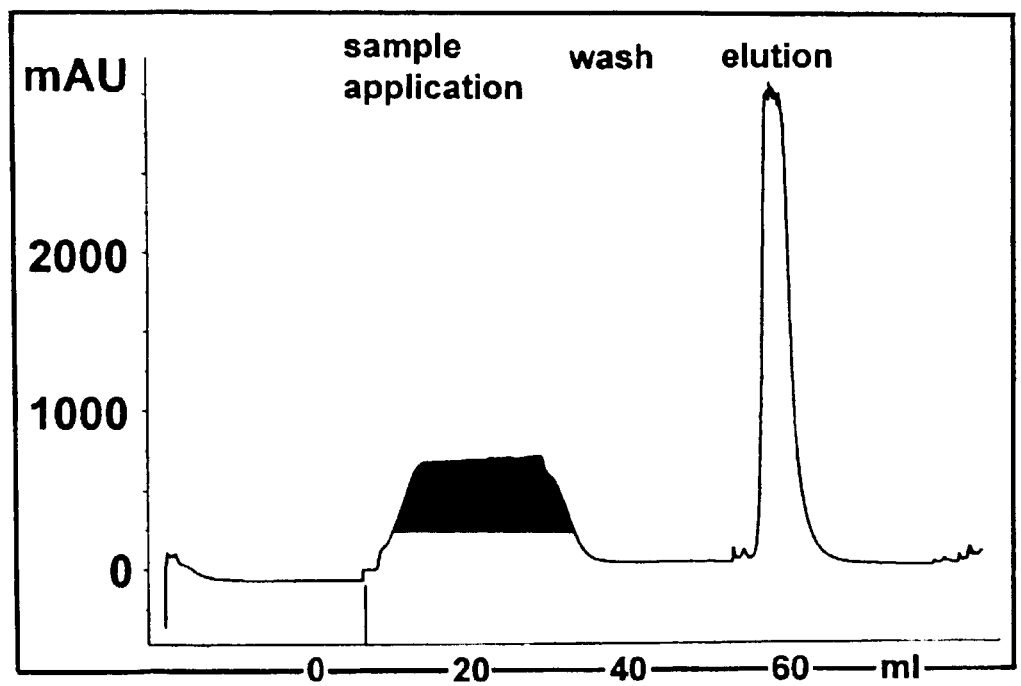
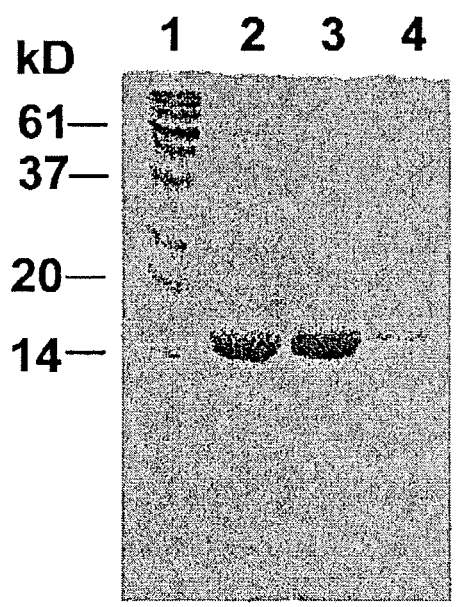
Fig.2 C

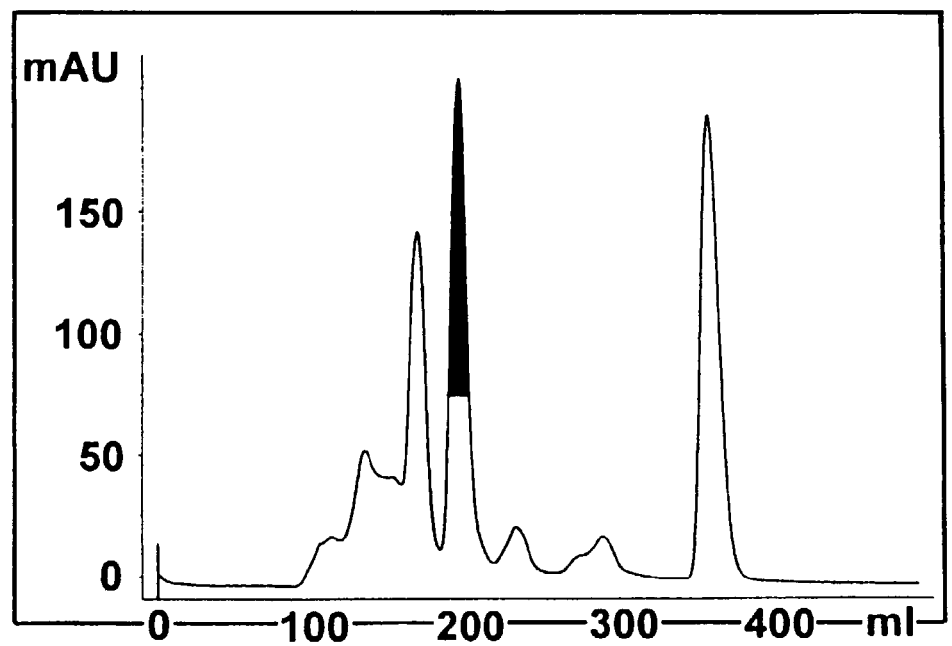
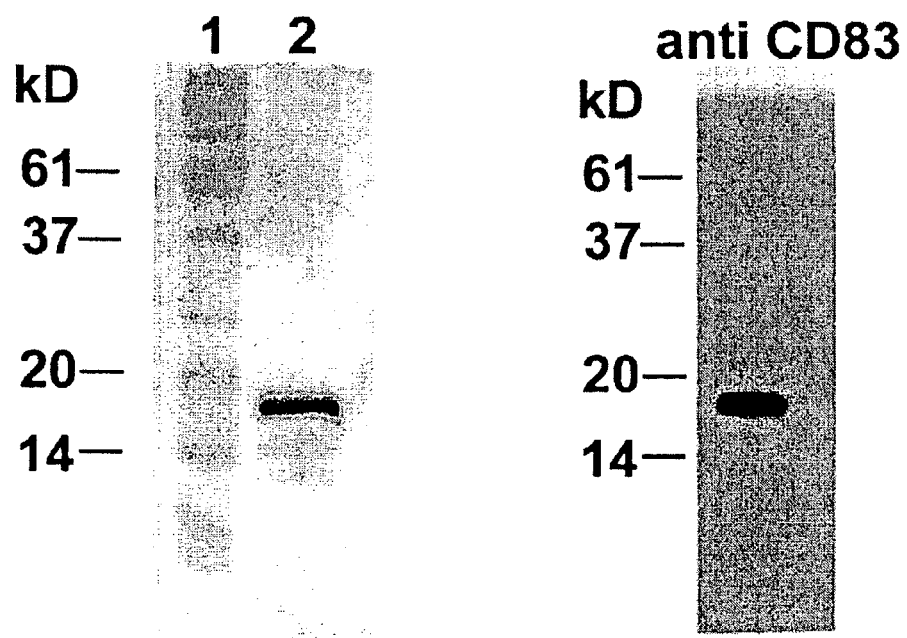
Fig. 2 D

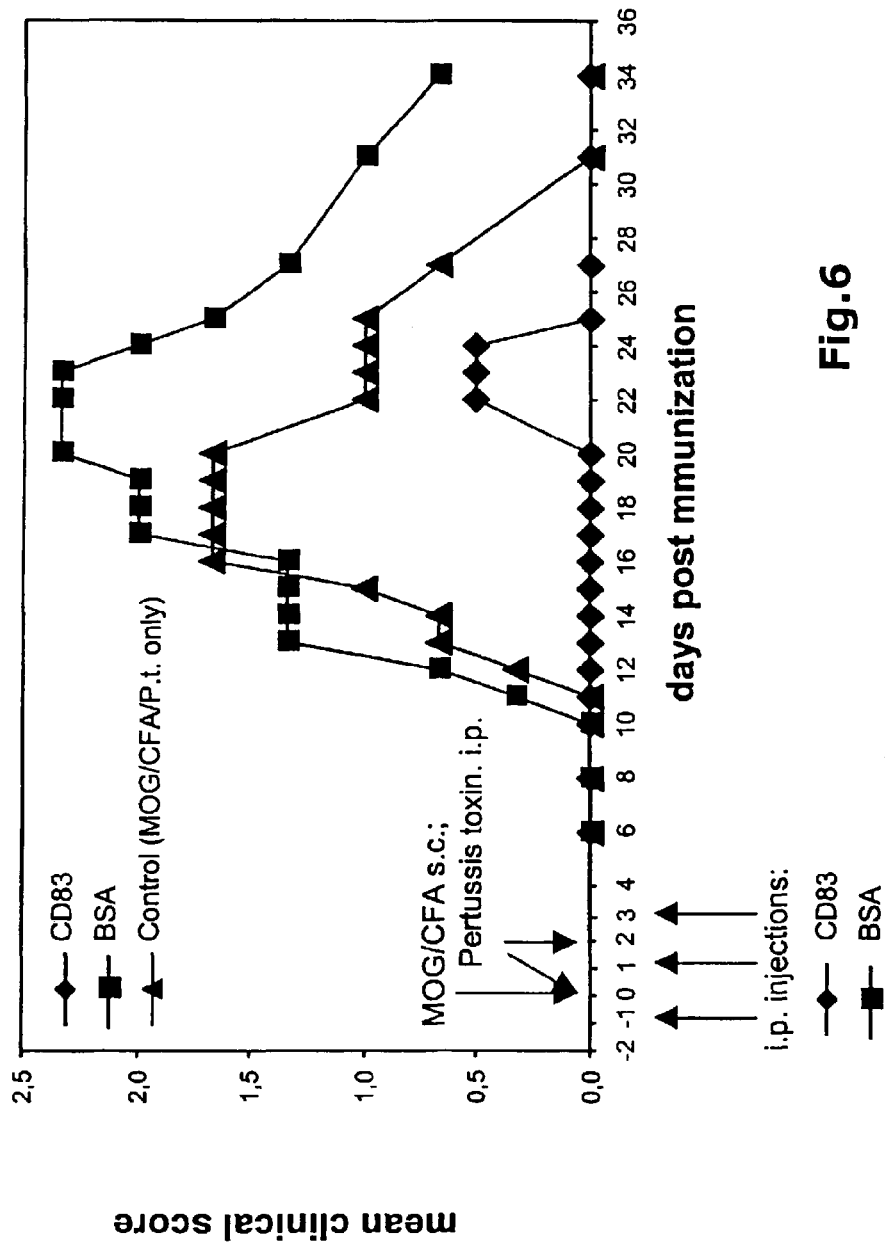

NUCLEIC ACID OF RECOMBINATION EXPRESSION VECTOR ENCODING SOLUBLE FORMS OF CD83, HOST CELLS TRANSFORMED/TRANSFECTED THEREWITH AND PHARMACEUTICAL COMPOSITIONS CONTAINING SAME

This application is a continuation-in-part of U.S. application Ser. No. 10/309,611, filed on Dec. 4, 2002 now U.S. Pat. No. 7,169,898.

The present invention provides for the use of soluble forms of CD83 and nucleic acids encoding them for the treatment of diseases caused by the dysfunction or undesired function of a cellular immune response involving T cells. The invention moreover provides soluble CD83 molecules specifically suited for said purpose, antibodies against said specific soluble CD83 proteins and assay methods and kits comprising said antibodies.

BACKGROUND OF THE INVENTION

The immune system of mammals must possess the capability to react to a very large number of foreign antigens. Lymphocytes constitute a central element of the immune system because they can recognize antigens and effect a specific, adaptive immune response. Lymphocytes can be divided into two general classes of cells, B-lymphocytes, which are capable of expressing antibodies, and T lymphocytes that can be sub-divided into CD4+ helper T cells and CD8+ cytotoxic T cells. Both of these sub-groups of T lymphocytes are capable of recognizing antigens associated with surface proteins known as the major histocompatibility complex (MHC). The recognition of the MHC occurs throughout the T cell receptor (TCR), a protein complex that is anchored in the cytoplasmic membrane of T cells. The CD8+ T cell receptor exclusively mediates interactions between MHC class I antigens and cytotoxic T cells; the CD4+ T cell receptor exclusively mediates interactions between MHC class II antigens and helper T cells.

The triggering of an immune response does not exclusively progress from T cells alone, but rather, through the interaction of T cells with so-called antigen presenting cells (APCs, also known as accessory cells) and their surface markers (for example MHC II).

These accessory cells can be sub-divided into "simple" APCs whose function is to present antigens and "professional" APCs that, beside from presenting antigens, also have an accessory function in stimulating lymphocytes. APCs themselves do not have antigen specificity but serve as "nature's adjuvant" by presenting antigens to T cells. Aside from mononuclear phagocytes, dendritic cells (DC) are members of the APC type. In fact, DCs are the most potent APC known today and they are the only APC that are also able to stimulate naive T cells and are therefore called "natures adjuvants". As a result of their different characteristics and function, two types of dendritic cells have been classified to date: follicular dendritic cells (also known as lymphoid-related DCs) that are present in the lymph nodes, spleen and mucosa-associated lymph tissues and interdigitating dendritic cells (also known as myeloid derived DCs) that are found in the interstitial space of most organs, in T cell rich zones of the lymph nodes and spleen and are distributed throughout the skin where they are known as Langerhans cells.

Immature dendritic cells, i.e. DCs that are not fully capable of stimulating T cells, have the function of taking up antigens and processing them into MHC-peptide complexes. Stimuli such as TNF-alpha (tumor necrosis factor) and CD40L induce the maturation of dendritic cells and lead to a massive de novo synthesis of MHC class I and MHC class II molecules and to a migration of the DC, for example, from the interstitial space of the internal organs through the blood into the lymph nodes of the spleen and liver. Moreover, increased expression of co-stimulator molecules (for example, CD80, CD86) and adhesion molecules (for example, LFA3) occurs during the migration phase into the secondary lymphoid tissues. Mature DC stimulate T lymphocytes upon arrival in the T cell rich regions of the secondary lymphoid tissue by presenting peptide antigens within the context of MHC class I or MHC class II to these T cells. Depending on the conditions, DCs can stimulate the activation of a variety of T cells which, in turn, can bring about a differential response of the immune system. For example, as mentioned above, DCs that express MHC class I can cause cytotoxic T cells to proliferate and DCs that express MHC class II can interact with helper T cells. In the presence of mature DCs and the IL-12 that they produce, these T cells differentiate into Th1 cells that produce interferon-gamma.

Interferon-gamma and IL-12 serve together to promote T-killer cells. In the presence of IL-4, DCs induce T cells to differentiate into Th2 cells which secrete IL-5 and IL-4 that in turn activates eosinophils and assist B cells to produce antibodies (Banchereau, J. and Steinman, R. M. (1998) Nature 392: 245-252).

DCs can also induce a so-called mixed leukocyte reaction (MLR) in vitro, a model for allogenic T cell activation and graft rejection.

A typical feature of these MLR-assays is the formation of large DC-T cell-clusters. Addition of hCD83ext at day 1 strongly inhibited the typical cell cluster formation of DC and proliferating T cells (Lechmann, M. et al. (2001) J. Exp. Med. 194: 1813-1821).

Mature DC characteristically express, amongst others (e.g. MHC I and II, CD80/86, CD40) the marker molecule CD83 on their cell surface (Zhou, L.-J. and Tedder, T. F. (1995) J. Immunology, vol. 154: 3821-3835). This is one of the best markers for mature DC known today.

CD83, a molecule from the Ig superfamily of proteins, is a single chain, 43 kDa glycoprotein consisting of 205 amino acids (SEQ ID NO:2) in its immature form. The first 19 amino acids represent the signal peptide of CD83 and they are lost upon insertion of the protein into the membrane, leaving a 186 amino acid membrane spanning protein. The mature CD83 has an extracellular domain formed by amino acids 20 to 144 (SEQ ID NO:2), a transmembrane domain comprising amino acids 145 to 166 (SEQ ID NO:2), and cytoplasmic domain formed by amino acids 167 to 205 (SEQ ID NO:2). The extracellular domain has as structural feature a single Ig-like (V-type) domain, and is expressed very strongly on the cell surface of mature DC. The extracellular domain of the CD83 protein differs from the typical Ig-like domain in that it is encoded by at least two exons: one exon only codes for a half of the Ig-like domain, whereas the other exon encodes the membrane spanning domain (see Zhou, L.-J., Schwarting, R., Smith, H. M. and Tedder, T. F. (1999) J. Immunology, vol. 149: 735-742). The cDNA encoding human CD83 contains a 618 bp open reading frame (SEQ ID NO:1, see Genbank ID: Z11697 and Zhou, L.-J. et al, supra (1995)).

While the precise function of CD83 remains to be determined, it has been demonstrated that inhibition of CD83 cell surface expression on mature DC by interference with nuclear export of CD83 mRNA leads to a clear reduction in the capacity of these cells to stimulate T cells. (Kruse, M. et al. (2000) J. Exp. Med. 191: 1581-1589). Thus, CD83 appears to be required for DC function. Furthermore it was found that when a soluble form of CD83 was administerd to cells, the amount of CD83 expressed by the cells was reduced (mature dendritic cells) or the cells did not start to produce CD83 (immature dendritic cells). Since immature dendritic cells have no CD83 in/on their membrane, this observation lead to the conclusion, that soluble CD83 must interact with another cell (membrane) protein than CD83, i.e. a heterophilic interaction is suspected to occur between the soluble CD83 and an unidentified ligand (Lechmann, M. et al. (Dez. 17, 2001) J. Exp. Med. 194: 1813-1821and (June 2002) Trends in Immunology, Vol. 23(6):273-275). Evidence for the occurrence of soluble CD83 in vivo also exist. Soluble CD83 has been found in normal human sera and and seems to be released from activated dendritic cells and B-lymphocytes (Hock et al. (2001) Int. Immunol. 13: 959-967).

WO 97/29781 relates to methods and compositions (vaccines) for stimulating a humoral immune response in which a soluble form of CD83 is employed as an adjuvant together with a given antigen. Soluble forms comprise CD83 fusion protein and a soluble form consisting of amino acids 1 to 124, the extracellular domain of CD83. In addition to the use of CD83 as adjuvant for vaccine preparations, this document discusses the use of antagonists (antibodies) against CD83 for inhibiting undesirable antigen specific responses in mammals.

WO 93/21318 describes a CD83 protein here designated HB15, chimeric HB15 molecules and HB15 fragments including a fragment consisting of the extracellular domain (amino acids 1 to 125) of HB15. Furthermore antibodies against HB15 usable as pharmaceuticals are revealed. Because of the role of HB15 as an accessory molecule for lymphocyte activation, the soluble HB15 and fragments is thought to be useful as an agonist for augmentation of the immune response.

U.S. Pat. No. 5,710,262 and the corresponding WO 95/29236 reveal human and mouse HB15 as potentially useful drug in the treatment of AIDS (with regard to the DNA and amino acid sequence of mouse HB15, see SEQ ID Nos:3 and 4). The extracellular domain of HB15 as described therein comprises the first 19 amino acids of the signal peptide, followed by 106 amino acids of the extracellular domain.

The above-mentioned WO 93/21318 and WO 95/29236 also emphasize that monoclonal antibodies against CD83 are suitable for removing endogenous CD83 or monitor CD83 levels in serum.

It was surprisingly found that the extracellular domain of CD83 (hereinafter also "hCD83ext") comprising amino acids 20 to 144 (SEQ ID NO:2), can engage in heterophilic interactions with ligands on dendritic cells. Since the current literature only describes complete extracellular domains or extracellular domains lacking amino acids from the C-terminus of the extracellular domain (U.S. Pat. No. 5,710,262, WO 95/29236 and WO 97/29781) it was also surprising that hCD83ext adopted the correct confirmation, allowing interactions with dendritic cells. Of even greater surprise was the effect hCD83ext had on dendritic cells; it prevented maturation of immature dendritic cells and reduced the expression of CD83 in mature dendritic cells. As a result dendritic cells lost their ability to activate T cells. Thus, the soluble hCD83ext itself was shown to be sutiable for the treatment or prevention of diseases or medical conditions caused by undesirable immune responses, in particular by preventing activation of T cells. hCD83ext was also found suitable for the treatment or prevention of diseases or medical conditions caused by undesirable immune responses mediated by dendritic cells and T cells.

It was found that due to the fact that the hDC83ext possesses the correct conformation of natural CD83, it is also suitable or preparing antibodies against CD83 (see Lechmann et al., Protein Expression and Purification 24, 445-452 (Mar. 5, 2002)).

Finally, it was found that the amount of soluble CD83 protein in the human serum varies and is significantly higher in case of tumors and B-cell leukemia. Thus, antibodies against the soluble CD83 protein are powerful tools for determining certain diseases (such as tumor, autoimmune diseases, viral infection, etc.) in a patient.

SUMMARY OF THE INVENTION

Extraordinarily, soluble hCD83ext can engage with immature and mature dendritic cells, preventing maturation of the immature dendritic cells. Furthermore, mature dendritic cells treated with soluble hCD83ext are completely inhibited in their T cell stimulatory activity. Thus T cells do not proliferate anymore. CD83 has been recognized as a marker for mature dendritic cells capable of T-cell interaction. Formerly mature and active dendritic cells treated with soluble hCD83ext are unable to form clusters with T cell in vitro. Hence the dendritic cells cannot induce anymore the division/stimulation of T cells.

As a result, the invention provides the use of a soluble form of a member of the CD83 family of proteins are suitable for the treatment or prevention of a disease or medical condition caused by the dysfunction or undesired function of a cellular immune response involving T cells. In particular, the soluble forms of a member of the CD83 family of proteins inhibit the interaction between dendritic cells and T cells.

Moreover, specific soluble CD83 proteins are provided which are suitable for the diseases defined above. Said soluble CD83 proteins were found to be particular suited for raising antibodies against CD83 proteins.

Finally, the invention provides that such antibodies are suitable in assays for determining diseases correlated with an enhanced precursor of soluble CD83 protein in the patient's serum.

More specifically the present invention provides
(1) the use of a soluble form of a member of the CD83 family of proteins (hereinafter shortly "soluble CD83 protein") or a fragment or a functional derivative thereof, for the production of a medicament for the treatment or prevention of a disease or medical condition caused by the dysfunction or undesired function of a cellular immune response involving T cells;
(2) the use of (1) above, wherein the medicament is suitable for the treatment or prevention of paralysis, preferably for the treatment or prevention of paralysis associated with progressive multiple sclerosis;
(3) the use of a nucleic acid or vector having a DNA fragment encoding a CD83 protein as defined in (1) or (2) above for the production of a medicament for the treatment or prevention of a disease or medical condition caused by the dysfunction or undesired function of a cellular immune response involving T cells;
(4) the use of (1) and (3) above, wherein said disease or medical condition caused by the dysfunction or undesired function of a cellular immune response involving T cells is selected from the group consisting of allergies, asthma, rejection of a tissue or organ transplant, autoimmune syndromes such as myasthemia gravis, multiple sclerosis, vasculitis, cronic inflammatory bowl diseases such as Morbus Crohn or colitis ulcerosa, HLA B27-associated autoimmunopathis such as Morbus Bechterew, and systemic lupus erythematosis, skin diseases such as psoriasis, rheumatoid arthritis, insulin-dependent diabetes mellitus and AIDS;

(5) a soluble form of a member of the CD83 family of proteins comprising amino acids 20 to 144 of SEQ ID NO:2 or a fragment or derivative thereof;

(6) a nucleic acid or recombinant expression vector encoding the CD83 protein of (5) above;

(7) a prokaryotic or eukaryotic host cells transformed/transfected with a nucleic acid or a vector of (6) above;

(8) a method for producing the soluble CD83 protein of (5) above, which comprises culturing a transferred/transfected prokaryotic or eukaryotic host cell according to (7) above;

(9) a pharmaceutical composition comprising the CD83 protein of (5) above;

(10) an antibody against a soluble CD83 protein as defined in (5) above;

(11) an assay method for in vitro determining the amount of soluble CD83 protein in the serum of a patient which comprises contacting a serum sample with the antibody of (10) above; and

(12) a kit for performing the assay method of (11) above and comprising the antibody of (10) above.

DESCRIPTION OF THE FIGURES

FIG. 1: Partial sequence of pGEX2ThCD83ext vector. The sequence of the extracellular CD83 domain is shown in bold letters. The amino-acid sequence "GSPG" was added to the N-terminus of the extracellular CD83 domain and is part of the thrombin cleavage site which is underlined. The C-terminal amino acid "I" is part of the cytoplasmic domain of CD83. SmaI and EcoRI cloning sites are indicated by a broken line (--).

FIG. 2: Purification of hCD83ext. A-D show the chromatographic elution profiles of the 4 purification steps. The collected aliquots are depicted in black. Proteins of the collected fractions were electrophoresed using a 15% polyacrylamid gel under reducing and denaturing conditions and visualized with Coomassie brilliant blue staining. In addition, D also shows Western blot analysis. A: Affinity chromatography using a GSTrap column: Lane 1: molecular weight marker (MWM); Lanes 4-10: aliquots of GST-hCD83ext. B: Anion exchange chromatography using a Source 15QPE 4.6/100 column: Lane 1: MWM; Lanes 2-7 aliquots of GST-hCD83ext. C: purification of the thrombin cleavage products using GSTrap-affinity chromatography: Lane 1: MWM; Lanes 2-4: collected flowthrough containing the cleaved hCD83ext. D: Gel filtration using a Superdex 75 (26/16) column: Lane 1: MWM; Lane 2: hCD83ext. The right panel shows the Western blot analyses using an anti-CD83 antibody.

FIG. 6: hCD83ext inhibits murine experimental autoimmune enzephalomyelitis (EAE) a in vivo model for multiple sclerosis (MS).

DETAILED DESCRIPTION OF THE INVENTION

Figure 3:
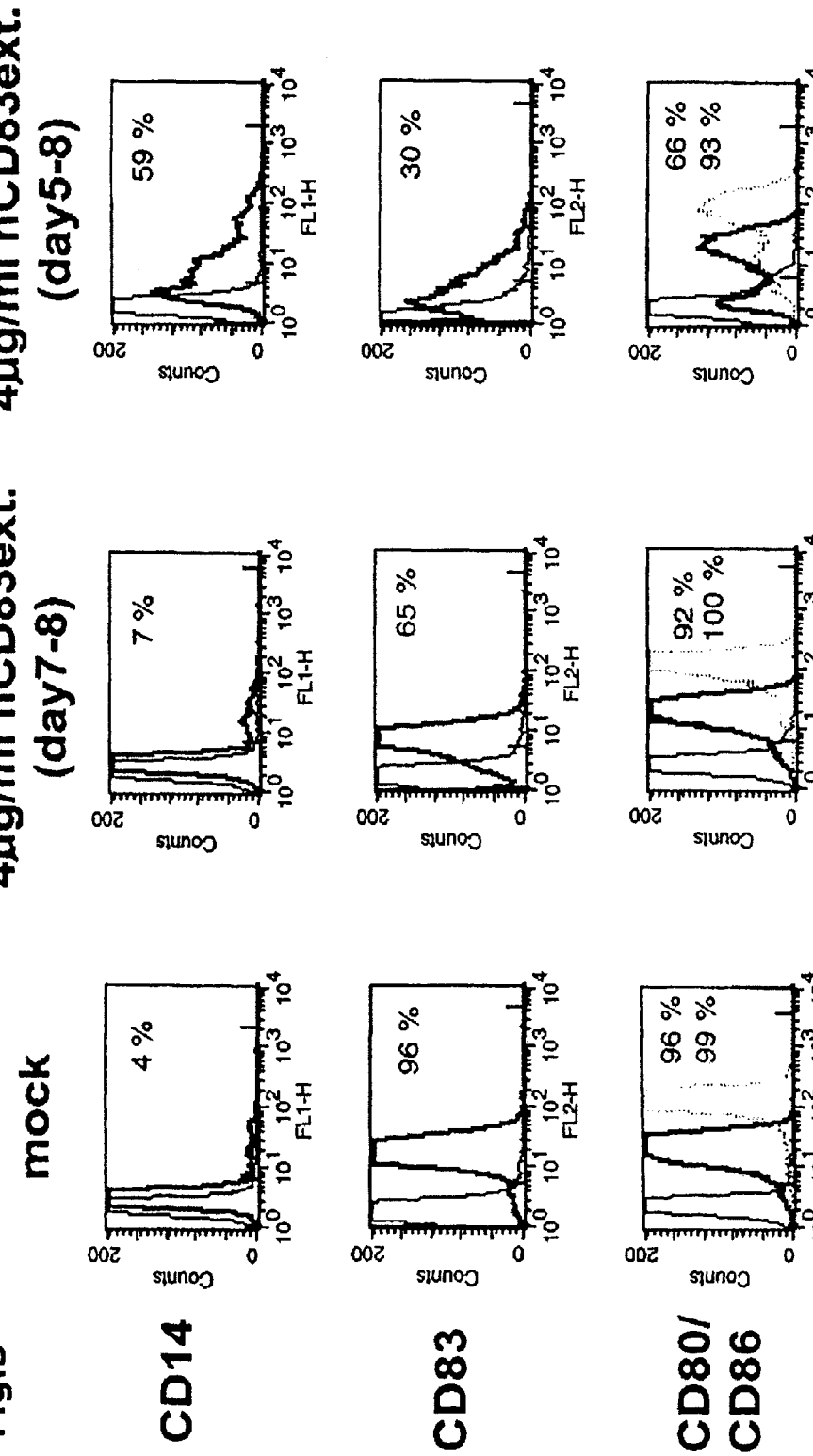
FIG. 3: FACS analyses of DC. A: immature DC where matured in the presence of the maturation cocktail from day 5-8 (=mock control for mature DC). B: immature DC where matured in the presence of the maturation cocktail (day 5-8) and on day 7 hCD83ext was added for 24 hours. C: immature DC where incubated in the presence of the maturation cocktail in combination with hCD83 from day 5-8. On day 8 cells where washed and stained with the indicated antibodies and analyzed by FACS

Using a PCR strategy the extracellular domain of CD83 plus the first codon of the cytoplasmic domain were amplified from a full-length human cDNA clone and inserted behind the gluthathione-transferase gene into an expression vector. In the resulting fusion protein the N-terminal glutathione-transferase (GST) was separated by a thrombin cleavage site from the extracellular CD83 domain extended by the Ile from the cytoplasmic domain. The fusion protein was purified from an overnight bacterial culture, subjected to thrombin cleavage and the hCD83ext further purified. The purified hCD83ext was used in dendritic cell maturation and T-cell stimulation (MLR) assays. Surprisingly, addition of hCD83ext to immature dendritic cells induced an altered surface marker expression pattern. CD80 expression was reduced from 96 to 66% and CD83 expression from 96 to 30%. Also mature dendritic cells changed the surface marker expression pattern upon exposure to hCD83ext. CD83 expression was reduced from 96 to 66%. Dendritic cells treated with hCD83ext lost their ability to stimulate T-cell proliferation. These results suggested a potential use of hCD83ext for treatment of T-cell mediated diseases and conditions. Therefore the effects of hCD83ext on Experimental Autoimmune Enzephalomyelitis (EAE), a model for Multiple Sclerosis, were studied. Surprisingly, the mice treated with hCD83ext did not develop the typical paralysis associated with EAE.

Hence according to embodiment (1) of the invention the soluble form of a member of the CD83 family of proteins, a fragment thereof, or a functional derivative thereof may be used for the production of a medicament for the treatment or prevention of a disease or medical condition caused by the dysfunction or undesired function of a cellular immune response involving T cells. Preferably soluble CD83 protein comprises at least amino acid residues 20 to 144, or 20 to 145 of SEQ ID NO: 2. Suitable fragments are those having the same activity and conformation as natural CD83. Suitable derivatives include, but are not limited to, those proteins having additional sequences attached to its C- or N-terminus, e.g. those carrying part of a transmembrane domain at their C-terminus or carrying at there N-terminus a short functional peptide (Gly-Ser-Pro-Gly) may be used. The medicaments containing these proteins and fragments are useful for the treatment or prevention of paralysis, as for example seen with progressive multiple sclerosis. In a similar manner, nucleic acids or vectors coding for these proteins or fragments thereof may be used in the production of medications for the treatment and prevention of medical conditions caused by the dysfunction or undesired function of cellular immune responses involving T cells. In particular DNA sequences comprising nucleotides 58 to 432, more preferably 58 to 435 of SEQ ID NO: 1 may be used. These medicaments may be used for the downregulation on RNA and/or protein level of the expression of CD83 in mammals. The use of these medicaments for the prevention or treatment of diseases such as allergies, asthma, rejection of a tissue or organ transplant, autoimmune syndromes such as myasthemia gravis, multiple sclerosis, vasculitis, cronic inflammatory bowl diseases such as Morbus Crohn or colitis ulcerosa, HLA B27-associated autoimmunopathis such as Morbus Bechterew, and systemic lupus erythematosis, skin diseases such as psoriasis, rheumatoid arthritis, insulin-dependent diabetes mellitus and AIDS may be appropriate. Methods of treatment and/or prevention of medical conditions caused by dysfunction or undesired T cell function may comprise administering an effective amount of CD83 or fragments as described herein; a method might also comprise administering an effective amount of a nucleic acid or vector as described above; the methods might be applied for the treatment or prevention of diseases such as allergies, asthma, rejection of a tissue or organ transplant, autoimmune syndromes such as myasthemia gravis, multiple sclerosis, vasculitis, cronic inflammatory bowel diseases such as Morbus Crohn or colitis ulcerosa, HLA B27-associated autoimmunopathis such as Morbus Bechterew, and systemic lupus erythematosis, skin diseases such as psoriasis, rheumatoid arthritis, insulin-dependent diabetes mellitus and AIDS.

As defined herein, the term "inhibit the interaction" is used to indicate that the soluble forms of the members of the CD83 family of proteins of the present invention are capable of disrupting the interaction of dendritic cells to T cells and/or the formation of dendritic cell-T cell clusters in vitro at physiological pH and salt concentrations, preferably, at pH concentrations ranging from pH 6.0 to 8.0 and/or at salt concentrations ranging from 50 mM to 250 mM, preferably 125 mM to 175 mM.

A preferred assay for determining the binding of dendritic cells to T cells and the formation of dendritic cell-T cell clusters is provided in the Examples (Lechmann, M. et al. (2001) J. Exp. Med. 194: 1813-1821).

The soluble forms of the members of the CD83 family of proteins for use in the present invention are capable of causing a disruption in the binding of dendritic cells to T cells and/or the formation of dendritic cell-T cell clusters of at least 25%, more preferably at least 50%, still more preferably at least 75% and most preferably at least 90% or greater as measured in the one of the above assays. The term "soluble form" of the CD83 family of proteins is used here to define a proteinaceous molecule that has at least a portion of the extracellular domain of a member of the CD83 family of proteins, but does not have an amino acid sequence that is capable of anchoring said molecule to the membrane of a cell in which it is expressed. The nucleic acid sequence encoding human CD83 protein as well as the amino acid sequence of CD83 are described in Zhou, L. J. et al. (1992) 3. Immunol. 149(2): 735-742 (Genbank accession number Z11697) and are provided in SEQ ID NO:1 and SEQ ID NO:2 respectively.

As defined herein, a member of the CD83 family of proteins includes any naturally occurring protein that has at least 70%, preferably 80%, and more preferably 90% or more amino acid identity to the human CD83 as depicted in SEQ ID NO:2.

Thus, aside from human CD83 itself, members of the CD83 family of proteins include the mouse HB15 protein that is encoded by the nucleic acid sequence of SEQ ID NO:3 and is represented by the amino acid sequence provided in SEQ ID NO:4, (Genbank accession number NM_009856 (Berchthold et al).

Other naturally occurring members of the CD83 family of proteins can be obtained by hybridizing a nucleic acid comprising, for example, all or the extracellular portion of the human CD83 coding region or mouse HB15 coding region to various sources of nucleic acids (genomic DNA, cDNA, RNA) from other animals, preferably mammals, or from other tissues of the same organism.

Hybridization refers to the binding between complementary nucleic acid sequences (e.g., sense/antisense). As is known to those skilled in the art, the Tm (melting temperature) refers to the temperature at which the binding between sequences is no longer stable. As used herein, the term "selective hybridization" refers to hybridization under moderately stringent or highly stringent conditions, which can distinguish CD83 related nucleotide sequences from unrelated sequences.

In nucleic acid hybridization reactions, the conditions used in order to achieve a particular level of stringency will vary, depending on the nature of the nucleic acids being hybridized. For example, the length, degree of sequence complementarity, sequence composition (e.g., the GC v. AT content), and type (e.g., RNA v. DNA) of the hybridizing regions can be considered in selecting particular hybridization conditions. An additional consideration is whether one of the nucleic acids is immobilized, for example, on a filter.

In general, the stability of a nucleic acid hybrid decreases as the sodium ion decreases and the temperature of the hybridization reaction increases. An example of moderate stringency hybridization reaction is as follows: 2×SSC/0.1 SDS at about 37° C. or 42° C. (hybridization conditions); 0.5×SSC/0.1% SDS at about room temperature (low stringency wash conditions); 0.5×SSC/0.1% SDS at about 42° C. (moderate stringency wash conditions). An example of high stringency hybridization conditions is as follows: 2×SSC/0.1% SDS at about room temperature (hybridization conditions); 0.5×SSC/0.1% SDS at about room temperature (low stringency wash conditions); 0.5×SSC/0.1% SDS at about 42° C. (moderate stringency wash conditions); and 0.1×SSC/0.1% SDS at about 65° C. (high stringency conditions).

Typically, the wash conditions are adjusted so as to attain the desired degree of stringency. Thus, hybridization stringency can be determined, for example, by washing at a particular condition, e.g., at low stringency conditions or high stringency conditions, or by using each of the conditions, e.g., for 10-15 minutes each, in the order listed above, repeating any or all of the steps listed. Optimal conditions for selective hybridization will vary depending on the particular hybridization reaction involved, and can be determined empirically.

Once a nucleic acid encoding a naturally occurring CD83 protein has been cloned, the extracellular domain can be determined by comparison of the extracellular domain of known CD83 molecules with that of the cloned CD83 sequence. A soluble form of a given naturally occurring CD83 protein can then be expressed recombinantly using the techniques as described herein. For example, a nucleic acid encoding a soluble form of CD83 can be produced, inserted into a vector and transformed into prokaryotic or eukaryotic host cells using well known techniques described herein and further known in the art (Sambrook et al. Molecular Cloning: A Laboratory Manual, Cold Spring Harbor Laboratory, N.Y., 1989).

Thus, when cloning in bacterial systems, constitutive promoters such as T7 and the like, as well as inducible promoters such as pi, of bacteriophage X, plac, ptrp, ptac (ptrp-lac hybrid promoter) may be used. When cloning in mammalian cell systems, constitutive promoters such as SV40, RSV, CMV including CMV-IE, and the like or inducible promoters derived from the genome of mammalian cells (e.g., metallothionein promoter) or from mammalian viruses (e.g., the mouse mammary tumor virus long terminal repeat; the adenovirus late promoter) may be used. Promoters produced by recombinant DNA or synthetic techniques may also be used to provide for transcription of the nucleic acid sequences of the invention.

Mammalian expression systems which utilize recombinant viruses or viral elements to direct expression may be engineered. For example, when using adenovirus expression vectors, nucleic acid of interest may be ligated to an adenovirus transcription/translation control complex, e.g., the late promoter and tripartite leader sequence. Alternatively, the vaccinia virus 7.5K promoter may be used.

Of particular interest are vectors based on bovine papilloma virus (BPV) which have the ability to replicate, as extrachromosomal elements. Shortly after entry of an extrachromosomal vector into mouse cells, the vector replicates to about 100 to 200 copies per cell. Because transcription of the inserted cDNA does not require integration of the plasmid into the host's chromosome, a high level of expression occurs. These vectors can be used for stable expression by including a selectable marker in the plasmid, such as the neo gene, for example. Alternatively, the retroviral genome can be modified for use as a vector capable of introducing and directing the expression of the nucleic acid of interest in host cells. High level expression may also be achieved using inducible promoters, including, but not limited to, the metallothionein RA promoter and heat shock promoters.

In yeast, a number of vectors containing constitutive or inducible promoters may be used. A constitutive yeast promoter such as ADH or LEU2 or an inducible promoter such as GAL may be used. Alternatively, vectors that facilitate integration of foreign nucleic acid sequences into a yeast chromosome, via homologous recombination for example, are known in the art and can be used.

A nucleic acid of interest encoding a soluble form of a member of the CD83 family of proteins for use according to the present invention may be inserted into an expression vector for expression in vitro (e.g., using in vitro transcription/translation assays or commercially available kits), or may be inserted into an expression vector that contains a promoter sequence which facilitates transcription and/or translation in either prokaryotes or eukaryotes (e.g., an insect cell) by transfer of an appropriate nucleic acid into a suitable cell. A cell into which a vector can be propagated and its nucleic acid transcribed, or encoded polypeptide expressed, is referred to herein as a "host cell".

The term also includes any progeny of the subject host cell. Moreover, a nucleic acid of interest according to the present invention may be inserted into an expression vector for expression in vivo for somatic gene therapy. With these vectors, for example, retroviral vectors, Adenovirus vectors, Adeno-associated virus vectors, plasmid expression vectors, the nucleic acids of the invention are expressed upon infection/introduction of the vector into DC.

Host cells include but are not limited to microorganisms such as bacteria, yeast, insect and mammalian organisms. For example, bacteria transformed with recombinant bacteriophage nucleic acid, plasmid nucleic acid or cosmid nucleic acid expression vectors containing a nucleic acid of interest; yeast transformed with recombinant yeast expression vectors containing a nucleic acid of interest; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a nucleic acid of interest; insect cell systems infected with recombinant virus expression vectors (e.g., baculovirus) containing a nucleic acid of interest; or animal cell systems infected with recombinant virus expression vectors (e.g., retroviruses, adenovirus, vaccinia virus) containing a nucleic acid of interest, or transformed animal cell systems engineered for stable expression.

For long-term expression of the soluble forms of members of the CD 83 family of proteins in host cells, stable expression is preferred. Thus, using expression vectors which contain viral origins of replication, for example, cells can be transformed with a nucleic acid of interest controlled by appropriate control elements (e.g., promoter/enhancer sequences, transcription terminators, polyadenylation sites, etc.). Optionally, the expression vector also can contain a nucleic acid encoding a selectable or identifiable marker conferring resistance to a selective pressure thereby allowing cells having the vector to be identified, grown and expanded. Alternatively, the selectable marker can be on a second vector that is cotransfected into a host cell with a first vector containing an invention polynucleotide.

A number of selection systems may be used, including, but not limited to the herpes simplex virus thymidine kinase gene, hypoxanthine-guanine phosphoribosyltrans-ferase gene, and the adenine phosphoribosyltransferase genes can be employed in tk-, hgprt or aprt cells respectively. Additionally, antimetabolite resistance can be used as the basis of selection for dhfr, which confers resistance to methotrexate; the gpt gene, which confers resistance to mycophenolic acid; the neomycin gene, which confers resistance to the aminoglycoside G-418; and the hygromycin gene, which confers resistance to hygromycin. Additional selectable genes have been described, namely trpB, which allows cells to utilize indole in place of tryptophan; hisD, which allows cells to utilize histinol in place of histidine; and ODC (ornithine decarboxylase) which confers resistance to the ornithine decarboxylase inhibitor, 2-(difluoromethyl)-DL-onithine, DFMO.

As used herein, the term "transformation" means a genetic change in a cell following incorporation of DNA exogenous to the cell. Thus, a "transformed cell" is a cell into which (or a progeny of which) a DNA molecule has been introduced by means of recombinant DNA techniques.

Transformation of a host cell with DNA may be carried out by conventional techniques known to those skilled in the art. For example, when the host cell is a eukaryote, methods of DNA transformation include, for example, calcium phosphate co-precipitates, conventional mechanical procedures such as microinjection, electroporation, insertion of a plasmid encased in liposomes, and viral vectors. Eukaryotic cells also can be cotransformed with DNA sequences encoding a nucleic acid of interest, and a second foreign DNA molecule encoding a selectable phenotype, such as the those described herein. Another method is to use a eukaryotic viral vector, such as simian virus 40 (SV40) or bovine papilloma virus, to transiently infect or transform eukaryotic cells and express the protein.

Following transformation, the soluble form of CD83 may be isolated and purified in accordance with conventional methods. For example, lysate prepared from an expression host (e.g., bacteria) can be purified using HPLC, size-exclusion chromatography, gel electrophoresis, affinity chromatography, or other purification technique. Substantially pure proteins can also be obtained by chemical synthesis using a peptide synthesizer (e.g. Applied Biosystems, Inc., Foster City, Calif.; Model 430A or the like).

The compounds for use in the present invention also include derivatives of soluble forms of members of the CD83 family of proteins according to the invention as mentioned above in which one or more amino acids has been added, deleted, substituted, inserted or inverted as long as these derivatives remain soluble as defined above and are capable of causing a disruption in the binding of dendritic cells to T cells and/or the formation of dendritic cell-T cell clusters as defined above.

When one or more amino acids of a soluble form of a member of the CD83 family of proteins is substituted, it is preferred that the one or more amino acids are conservatively substituted. For example, conservative substitutions include substitutions in which aliphatic amino acid residues such as Met, Ile, Val, Leu or Ala are substituted for one other. Likewise, polar amino acid residues can be substituted for each other such as Lys and Arg, Glu and Asp or Gln and Asn.

According to the invention, derivatives of a soluble form of a member of the CD83 family of proteins also include derivatives in which one or more of the amino acids therein has an altered side chain. Such derivatized polypeptides include, for example, those comprising amino acids in which free amino groups form amine hydrochlorides, p-toluene sulfonyl groups, carobenzoxy groups; the free carboxy groups form salts, methyl and ethyl esters; free hydroxl groups that form O-acyl or O-alkyl derivatives as well as naturally occurring amino acid derivatives, for example, 4-hydroxyproline, for proline, 5-hydroxylysine for lysine, homoserine for serine, ornithine for lysine etc. Also included are amino acid derivatives that can alter covalent bonding, for example, the disulfide linkage that forms between two cysteine residues that produces a cyclized polypeptide.

A soluble form of a member of the CD83 family of proteins or derivatives thereof can have a native glycosylation pattern of a CD83 molecule or an altered glycosylation pattern or can be non-glycosylated as long as these molecules are soluble as defined above and are capable of causing a disruption in the binding of dendritic cells to T cells and/or the formation of dendritic cell-T cell clusters as defined above.

In a preferred embodiment, the soluble form of CD83 for use in the present invention comprises amino acids 20 to amino acids 144, more preferably amino acids 20 to 145, of the human CD83 protein as depicted in SEQ ID NO:2 or amino acids 1 to 130 of SEQ ID NO:8.

In a further preferred embodiment the soluble form of CD83 for use in the present invention comprises amino acids 22 to amino acids 135 of the mouse HB15 protein as depicted in SEQ ID NO:4.

The present invention also relates to the use of a nucleic acid or an expression vector encoding a soluble form of a member of the CD83 family of proteins or a derivative of such a protein for the production of a medicament for the treatment or prevention of a disease or medical condition caused by the dysfunction or undesired function of a cellular immune response involving T cells.

The nucleic acids for use in the present invention as described above can be in the form of DNA (deoxyribonucleic acid) which contains the bases adenine, thymine, guanine and cytosine or RNA (ribonucleic acid) which contains the bases adenine, uracil, guanine and cytosine or mixtures of the two.

When the nucleic acid molecule for use in the invention is derived from human CD83 protein, the portion of the coding region is preferably from nucleotide 58 to 432 of the sequence in SEQ ID NO:1. Alternatively, the portion of the coding region is from nucleotide 58 to 435 of the sequence in SEQ ID NO: 1.

When the nucleic acid molecule for use in the invention is derived from the mouse HB15 protein, the portion of the coding region is preferably from about nucleotide 76 to 418 of the sequence in SEQ ID NO:3.

A nucleic acid that encodes a protein for use according to the invention may be inserted into a vector. The term "vector" refers to a plasmid, virus or other vehicle known in the art that can be manipulated by insertion or incorporation of a polynucleotide. Such vectors can be used for genetic manipulation (i.e., "cloning vectors") or can be used to transcribe or translate the inserted polynucleotide ("expression vectors"). A vector generally contains at least an origin of replication for propagation in a cell and a promoter. Control elements, including expression control elements as set forth herein, present within an expression vector are included to facilitate proper transcription and translation (e.g., splicing signal for introns, maintenance of the correct reading frame of the gene to permit in-frame translation of mRNA and, stop codons etc.). The term "control element" is intended to include, at a minimum, one or more components whose presence can influence expression, and can also include additional components, for example, leader sequences and fusion partner sequences.

As used herein, the term "expression control element" refers to one or more nucleic acid sequence that regulates the expression of a nucleic acid sequence to which it is operatively linked. An expression control element operatively linked to a nucleic acid sequence controls transcription and, as appropriate, translation of the nucleic acid sequence. Thus an expression control element can include, as appropriate, promoters, enhancers, transcription terminators, a start codon (e.g., ATG) in front of a protein-encoding gene. "Operatively linked" refers to a juxtaposition wherein the components so described are in a relationship permitting them to function in their intended manner.

By "promoter" is meant a minimal sequence sufficient to direct transcription. Both constitutive and inducible promoters are included in the invention (see e.g. Bitter et al., Methods in Enzymology 153:516-544, 1987). Inducible promoters are activated by external signals or agents. Also included in the invention are those promoter elements which are sufficient to render promoter-dependent gene expression controllable for specific cell-types, tissues or physiological conditions; such elements may be located in the 5',3' or intronic regions of the gene. Promoters useful in the invention also include conditional promoters. A "conditional promoter" is a promoter which is active only under certain conditions. For example, the promoter may be inactive or repressed when a particular agent, such as a chemical compound, is present. When the agent is no longer present, transcription is activated or derepressed.

A nucleic acid of interest according to the present invention may be inserted into an expression vector for expression in vivo for somatic gene therapy. With these vectors, for example, retroviral vectors, Adenovirus vectors, Adeno-associated virus vectors, plasmid expression vectors, the nucleic acids of the invention are expressed upon infection/introduction of the vector into DC or T cells.

Furthermore, the invention relates to a method of treatment or prevention of a disease or medical condition caused by the dysfunction or undesired function of a cellular immune response involving T cells, wherein an effective amount of a soluble form of hCD83ext is administered to a subject.

Moreover, the invention relates to a method of treatment or prevention of a disease or medical condition caused by the dysfunction or undesired function of a cellular immune response involving T cells, wherein an effective amount of a nucleic acid or expression vector encoding a soluble hCD83ext is administered to a subject.

According to the invention, a soluble hCD83ext or a nucleic acid or expression vector encoding hCD83ext can be used to treat or prevent rejection of tissue and/or organ transplants, particularly xenogenic tissue and/or organ transplants, that occurs as a result of for example graft-vs.-host disease or host-vs.-graft disease.

In a further embodiment of the present invention, a soluble form of a member of the CD83 family of proteins or a nucleic acid or expression vector encoding a hCD83ext can be used to treat or prevent undesirable response to foreign antigens and therewith allergies and asthma or similar conditions.

Other disorders, diseases and syndromes that can be treated or prevented by the use of a soluble hCD83ext or a nucleic acid or expression vector encoding a soluble hCD83ext include autoimmune syndromes such as myasthemia gravis, multiple sclerosis, vasculitis, cronic inflammatory bowl diseases such as Morbus Crohn or colitis ulcerosa, HLA B27-associated autoimmunopathis such as Morbus Bechterew, and systemic lupus erythematosis, skin diseases such as psoriasis, rheumatoid arthritis, insulin-dependent diabetes mellitus and AIDS;

In particular hCD83ext is suitable for the treatment of paralysis associated with multiple sclerosis.

For therapeutic or prophylactic use, the compounds of the present invention alone, or in combination with other immune modulatory compounds, e.g. tolerance inducing antigens, are administered to a subject, preferably a mammal, more preferably a human patient, for treatment or prevention in a manner appropriate for the medical indication. Transcutan, intracutan, subcutan and/or systemic administration may be chosen for the delivery of hCD83ext and derivatives thereof.

The production of pharmaceutical compositions with an amount of one or more compounds according to the invention and/or their use in the application according to the invention occurs in the customary manner by means of common pharmaceutical technology methods. For this, the compounds according to the invention are processed together with suitable, pharmaceutically acceptable adjuvents and/or carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are among the most important systemically employed medicaments for the above mentioned indications. Preferably, injections are prepared either in the form of vials or also as so-called ready-to-use injection preparations, for example as ready-to-use syringes or single use syringes in addition to perforation bottles for multiple withdrawals. Administration of the injection preparations can occur in the form of subcutaneous (s.c.), intramuscular (i.m.), intravenous (i.v.), internodal (i.n.) or intracutaneous (i.e.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired dosage of the compounds of the invention. Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemulsions and liquids based on mixed micells, for example, based on phospholipids. As with injection preparations, infusion formulations can also be prepared in the form of concentrates to dilute. The injectable formulations can also be applied in the form of continuous infusions as in stationary as well as in out-patient therapy, for example in the form of mini-pumps.

Albumin, plasma expanders, surface active compounds, organic solvents, pH influencing compounds, complex forming compounds or polymeric compounds can be added to the parenteral medicinal forms with the aim of decreasing the adsorption of the compounds of the present invention to materials such as injection instruments or packaging materials, for example plastic or glass.

The compounds according to the invention can be bound to nanoparticles in the preparations for parenteral use, for example on finely dispersed particles based on poly(meth) acrylates, polyacetates, polyglycolates, polyamino acids or polyether urethanes. The parenteral formulations can also be constructively modified as depot preparations, for example on the multiple unit principle, where the compounds of the present invention are incorporated in a most finely distributed and/or dispersed, suspended form or as crystal suspensions, or on the single unit principle, where the compounds according to the invention are enclosed in a medicinal form, for example, a tablet or a seed which is subsequently implanted. Often, these implantation or depot medicaments in single unit and multiple unit medicinal forms consist of so-called biodegradable polymers, such as for example, polyether urethanes of lactic and glycolic acid, polyether urethanes, polyamino acids, poly(meth)acrylates or polysaccharides.

Sterilized water, pH value influencing substances, such as for example organic and inorganic acids or bases as well as their salts, buffer substances for setting the pH value, agents for isotonicity, such as for example sodium chloride, monosodium carbonate, glucose and fructose, tensides and/or surface active substances and emulsifiers, such as for example, partial fatty acid esters of polyoxyethylene sorbitan (Tween®) or for example fatty acid esters of polyoxethylene (Cremophor®), fatty oils such as for example peanut oil, soybean oil and castor oil, synthetic fatty acid esters, such as for example ethyl oleate, isopropyi myristate and neutral oil (Miglyol®) as well as polymer adjuvents such as for example gelatin, dextran, polyvinylpyrrolidone, organic solvent additives which increase solubility, such as for example propylene glycol, ethanol, N,N-dimethylacetamide, propylene glycol or complex forming compounds such as for example citrates and urea, preservatives, such as for example hydroxypropyi benzoate and hydroxymethyl benzoate, benzyl alcohol, anti-oxidants, such as for example sodium sulfite and stabilizers, such as for example EDTA, are suitable as adjuvents and carriers in the production of preparations for parenteral use.

In suspensions, addition of thickening agents to prevent the settling of the compounds of the present invention from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fatty acid esters. The compounds according to the invention can also be incorporated in liquid formulations in the form of inclusion compounds, for example with cyclodextrins. As further adjuvents, dispersion agents are also suitable. For production of lyophilisates, builders are also used, such as for example mannite, dextran, saccharose, human albumin, lactose, PVP or gelatin varieties.

A further systemic application form of importance is peroral administration as tablets, hard or soft gelatin capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized compounds of the present invention, diffusions and erosion forms based on matrices, for example by using fats, wax-like and/or polymeric compounds, or so-called reservoir systems. As a retarding agent and/or agent for controlled release, film or matrix forming substances, such as for example ethylcellulose, hydroxypropylmethylcellulose, poly (meth)acrylate derivatives (for example Eudragit®), hydroxypropylmethylcellulose phthalate are suitable in organic solutions as well as in the form of aqueous dispersions. In this connection, so-called bio-adhesive preparations are also to be named in which the increased retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of the compounds of the present invention, are especially suitable. For purposes of a targeted release of compounds of the present invention in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatin capsules.

Anti-stick and lubricant and separating agents, dispersion agents such as flame dispersed silicone dioxide, disintegrants, such as various starch types, PVC, cellulose esters as granulating or retarding agents, such as for example wax-like and/ or polymeric compounds on the basis of Eudragit®, cellulose or Cremophor® are used as a further adjuvants for the production of compressives, such as for example tablets or hard and soft gelatin capsules as well as coated tablets and granulates.

Anti-oxidants, sweetening agents, such as for example saccharose, xylite or mannite, masking flavors, aromatics, preservatives, colorants, buffer substances, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methylcellulose, hydroxypropylcellulose or silica, talcum powder, stearates, such as for example magnesium stearate, aluminum stearate, calcium stearate, talc, siliconized talc, stearic acid, acetyl alcohol and hydrated fats are used.

In this connection, oral therapeutic systems constructed especially on osmotic principles, such as for example GIT (gastrointestinal therapeutic system) or OROS (oral osmotic system), are also to be mentioned.

Effervescent tablets or tabs, both of which represent immediately drinkable instant medicinal forms which are quickly dissolved or suspended in water are among the perorally administratable compressives. Among the perorally administratable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspisated juices which are formulated with water before ingestion. Ion exchange resins in combination with one or more compounds of the present invention are also to be mentioned for the production of liquid ingestable forms.

A special release form consists in the preparation of so called floating medicinal forms, for example based on tablets or pellets which develop gas after contact with body fluids and therefore float on the surface of the gastric fluid. Furthermore, so-called electronically controlled release systems can also be formulated by which release of the compounds of the present invention can be selectively adjusted to individual needs.

A further group of systemic administration and also optionally topically effective medicinal forms are represented by rectally applicable medicaments.

Among these are suppositories and enema formulations. The enema formulations can be prepared based on tablets with aqueous solvents for producing this administration form. Rectal capsules can also be made available based on gelatin or other carriers.

Hardened fat, such as for example Witepsol®, Massa Estarinum®, Novata®, coconut fat, glycerol-gelatin masses, glycerol-soap-gels and polyethylene glycols are suitable as suppository bases.

For long-term application with a systematic release of the compounds of the present invention up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the compounds of the present invention in a controlled manner over longer or shorter time periods based on different layers and/or mixtures of suitable adjuvents and carriers. Aside from suitable adjuvents and carriers such as solvents and polymeric components, for example based on Eudragit®, membrane infiltration increasing substances and/or permeation promoters, such as for example oleic acid, Azone®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations: vaginally or genitally applicable emulsions, creams, foam tablets, depot implants, ovular or transurethral administration installation solutions. For opthalmological application, highly sterile eye ointments, solutions and/or drops or creams and emulsions are suitable.

In the same manner, corresponding otological drops, ointments or creams can be designated for application to the ear. For both of the above-mentioned applications, the administration of semi-solid formulations, such as for example gels based on Carbopols® or other polymer compounds such as for example polyvinylpyrolidone and cellulose derivatives is also possible.

For customary application to the skin or also to the mucus membrane, normal emulsions, gels, ointments, creams or mixed phase and/or amphiphilic emulsion systems (oil/water-water/oil mixed phase) as well as liposomes and transfersomes can be named. Sodium algenate as a gel builder for production of a suitable foundation or celluolose derivatives, such as for example guar or xanthene gum, inorganic gel builders, such as for example aluminum hydroxides or bentonites (so-called thixotropic gel builder), polyacrylic acid derivatives, such as for example Carbopol®, polyvinylpyrolidone, microcrystalline cellulose or carboxymethylcellulose are suitable as adjuvents and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and vaseline.

Anionic, cationic or neutral tensides can be employed as emulsifiers, for example alkalized soaps, methyl soaps, amine soaps, sulfanated compounds, cationic soaps, high fatty alcohols, partial fatty acid esters of sorbitan and polyoxyethylene sorbitan, for example lanette types, wool wax, lanolin, or other synthetic products for the production of oil/water and/or water/oil emulsions.

Hydrophilic organogels can be formulated, for example, on the basis of high molecular polyethylene glycols. These gel-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, Tris-buffer or triethanolamine are used for adjusting the pH value. Preservatives, for example such as methyl- or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base. Powders or topically applicable powders can contain for example starch varieties such as wheat or rice starch, flame dispersed silicon dioxide or silica, which also serve as diluents, for increasing flowability as well as lubricity as well as for preventing agglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administration of the compounds of the present invention.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated as invention compound-soft pellets, as an invention compound-pellet mixture with suitable carriers, such as for example lactose and/or glucose. For inhalation or insufflation, common applicators are suitable which are suitable for the treatment of the nose, mouth and/or pharynx. The compounds of the present invention can also be applied by means of an ultrasonic nebulizing device. As a propellant gas for aerosol spray formulations and/or controlled dosage aerosols, tetrafluoroethane or HFC 134a and/or heptafluoropropane or HFC 227 are suitable, wherein non-fluorinated hydrocarbons or other propellants which are gaseous at normal pressure and room temperature, such as for example propane, butane or dimethyl ether can be preferred. Instead of controlled dosage aerosols, propellant-free, manual pump systems can also be used.

The propellant gas aerosols can also suitably contain surface-active adjuvents, such as for example isopropyl myristate, polyoxyethylene sorbitan fatty acid ester, sorbitan trioleate, lecithins or soya lecithin.

In addition, when the pharmaceutical composition comprises a nucleic acid for use in the invention for administration to a certain species of animal, the nucleic acid for use in the invention is preferably derived from that species. For example, when the pharmaceutical composition is to be administered to humans, the nucleic acid of the pharmaceutical preferably comprises the soluble form of the human CD83 protein or a derivative thereof.

The nucleic acids for use in the invention can be administered in conjunction with agents that increase cell membrane permeability and/or cellular uptake of the nucleic acids. Examples of these agents are polyamines as described for example by Antony, T. et al. (1999) Biochemistry 38: 10775-10784; branched polyamines as described for example by Escriou, V. et al (1998) Biochem. Biophys. Acta 1368(2): 276-288; polyaminolipids as described for example by Guy-Caffey, J. K. et al. (1995) J. Biol. Chem. 270(52): 31391-31396; DOTMA as desribed by Felgner, P. L. et al. (1987) PNAS USA 84(21): 7413-7417 and cationic porphyrins as described for example by Benimetskaya, L. et al. (1998) NAR 26(23): 5310-5317.

According to embodiment (10) of the invention the above defined soluble CD83 is suitable for preparing antibodies (polyclonal or monoclonal) against CD83. The antibodies can be prepared according to standard methods known in the art. These antibodies are specifically useful for the assay method of embodiment (11) and the kit (12) of the invention. Said assay method is specifically suitable for determining diseases correlated with an enhanced presence of soluble CD83 protein in the patient's serum, preferably the method for determining tumor, autoimmune diseases, viral infections, etc., including B-Cell leukemia in a patient.

Using an Elisa test soluble CD83 was detected at a concentration of approx. 0.25 ng/ml (+/−0.25 ng/ml) in healthy individuals. Surprisingly, in tumor patients concentrations of up to 15 ng/ml were detected. Thus, this test could be of diagnostic and prognostic value for tumor patients. In addition also for patients suffering from autoimmune disorders, allergy and viral-, bacterial- and/or parasitic infenctions.

In the following, various aspects of the invention are more closely described via examples. However, the invention should not be considered as being to the examples.

EXAMPLES

Example 1

Recombinant Expression of Extracellular Human CD83 Domain in *Escherichia Coil*

Using a full-length human cDNA clone as a template, the extracellular domain of CD83 was PCR-amplified (PCR conditions: 1 cycle of 1 min at 94° C.; 30 cycles, each consisting of 1 min at 94° C. "denaturation", 1 min at 64° C. "annealing", 1 min at 72° C. "extension") using the following PCR primers:

5'-TCCCCGGGAACGCCGGAGGTGAAGGTGGCT-3'  (SEQ ID NO: 5)

-continued

5'-AATTAGAATTCTCAAATCTCCGCTCTGTATT-3'.   (SEQ ID NO: 6)

The amplified cDNA fragment was cloned into the SmaI and EcoRI sites of the expression vector pGEX2T (Amersham Pharmacia Biotech, Freiburg, Germany) resulting in the plasmid pGEX2ThCD83ext and this plasmid was transformed into the *E. coli* strain TOP10F' [F{lacI$^q$Tn10 (Tet$^R$)mcrA Δ(mrr-hsd RMS-mcrBC) φ80 lacZ, ΔM15 ΔlacX74 recA1 deoR araD139 Δ(ara-leu) 7697 galU galK rpsL(Str$^R$) endA1 nupG] (Invitrogen, Groningen, The Netherlands). The correct nucleotide sequence of pGEX2ThCD83ext was verified by sequencing. The extracellular CD83 was expressed as a fusion protein containing glutathione S-transferase as a fusion partner at the amino-terminus. A thrombin cleavage recognition site was inserted between GST and the extracellular CD83 domain (See FIG. 1).

Example 2

Purification of the Recombinant Human CD83ext

An overnight bacterial culture of the above-mentioned bacteria was diluted 1:10 in fresh LB medium (supplemented with 100 i-ig/ml ampicillin) and grown to an optical density of 1.0. IPTG was added (final concentration 1 mM) and the culture proceeded for a further hour. The cells were pelleted, resuspended in 10 ml native buffer (140 mM NaCl, 2.7 mM KCl, 10 mM $Na_2HPO_4$, 1.8 mM $KH_2PO_4$, 2.6 mM $MnCl_2$, 26 mM $MgCl_2$, 1 µg/ml leupeptin, 1 µg/ml aprotinin, 1 µg/ml DNAse I, pH 7.6) per 500 ml culture and 50 µg/ml lysozym were added. After 15 min incubation on ice the lysate was centrifuged at 20,000×g.

Capture Step:

40 ml of the supernatant were added to a GSTrap 5 ml column on a ÄKTA Explorer 10 system (Amersham Pharmacia Biotech, Uppsala, Sweden) that was previously equilibrated with 4 column volumes of binding buffer: PBS (phosphate buffered saline), pH 7.6. The column was then washed with 12 column volumes of the same binding buffer and subsequently eluted with 5 column volumes of elution buffer: 50 mM Tris-HCl, pH 8.0 with 5 mM reduced glutathione at a flow rate of 5 ml/min. The column was then treated with 5 column volumes of 2 M NaCl/PBS, pH7.6 and 5 column volumes of binding buffer (FIG. 2a).

Intermediate Purification Steps:

The GST-CD83ext-containing fractions were dialyzed against 50 mM 1-methyl-piperazine (Sigma), 50 mM Bis-Tris (Sigma), 25 mM Tris (Sigma) pH9.5 (buffer A) and loaded onto a 15Q PE 4.6/100 anion exchange column (Amersham Pharmacia Biotech) on a ÄKTA Explorer 10 system (Amersham Pharmacia Biotech). Proteins were separated by 3 different linear salt gradients: 16 column volumes to a target concentration of 10% buffer B (buffer A/1 M NaCl); 20 column volumes to a target concentration of 50% buffer B and 10 column volumes to a target concentration of 100% buffer B. (See FIG. 2b).

The GST-CD83ext-containing fractions were dialyzed against PBS, pH 7.6. Then, the GST-hCD83ext fusion protein was incubated with thrombin (20 U/ml) on a glutathione-Sepharose matrix at 22° C. for 16 h. To separate the hCD83ext protein from GST, this solution was loaded onto pre-packed glutathione-Sepharose 4B columns using the same buffer conditions as in the capture step. Under binding buffer conditions, the flow-through fraction containing recombinant human CD83ext protein was collected. The results are shown in FIG. 2c.

Polishing Step:

Finally, a preparative gel filtration separation was performed loading this flow-through fraction onto a Superdex 200 (26/16) prep grade column (Amersham Pharmacia Biotech) on a ÄKTA Explorer 10 system (Amersham Pharmacia Biotech) using a running buffer of PBS, pH7.6, at a flow rate of 3 ml/min.

The correct fractions were tested by silver staining, coomassie staining and Western blot analysis with anti-CD83 (Coulter-Immunotech, Marseilles, France) (See FIG. 2d).

Example 3

Inhibition of Dendritic Cell Maturation, in vitro Cell Cluster and MLR Experiments (Human)

Unless otherwise noted, all cells were cultured using a standard medium (1% human plasma medium), which consisted of RPMI 1640 (BioWhittaker, Verviers, Belgium) supplemented with glutamine (200 µg/mi) (BioWhittaker, Verviers, Belgium), penicillin/streptomycin (20 µg/ml), 10 mM Hepes, pH7.5 (Sigma-Aldrich), and 1% heat-inactivated (56° C.; 30 min) human plasma from a single donor obtained from the Department of Transfusion Medicine, Eriangen, Germany.

Generation of Dendritic Cells(DCs):

PBMCs were isolated from buffy coats by sedimentation in Ficoll-hypaque (Amersham Pharmacia Biotech, Freiburg, Germany) and seeded onto IgG-coated (10 µg/ml γ-globulin from Cohn fraction; Sigma-Aldrich) 100 mm-culture dishes and incubated at 37° C. in 5% $CO_2$. After 1 and 7 h incubations, non-adherent cell fractions were harvested, and the adherent cells were further cultured in 1% human plasma medium supplemented with the cytokines GM-CSF (800 U/ml) and IL-4 (500 U/ml). Fresh medium with GM-CSF to a final concentration of 400 U/ml and IL-4 (500 U/ml) was added on day 3 of the incubation period. On day 4 or 5, non-adherent cells were collected, counted, and transferred into new dishes at a density of 0.3-0.5×10$^5$ cells/mi. For final DC maturation, 1% human plasma medium was supplemented with TNF-α, (1.25 ng/ml), GM-CSF (40 U/ml), IL-4 (200 U/ml), prostaglandin $E_2$ (0.5 µg/ml). (Lechmann, M. et al. (2001) J. Exp. Med. 194: 1813-1821).

Soluble hCD83ext Inhibits Maturation of Immature Dendritic Cells

To analyze the influence of hCD83ext on the phenotype of DC, FACS analyses were performed on day 8 (See FIG. 3). DC can be fully matured with the use of a specific maturation cocktail composed of IL-1β, TNF-α and $PGE_2$ (FIG. 3a). Interestingly, when this maturation cocktail was administered to immature DC on day 5 together with hCD83ext (4 µg/ml) and left until the final FACS analyses on day 8, these cells revealed a clear reduction in CD80 (from 96% to 66%) and CD83 cell surface expression (96% to 30%) (FIG. 3c), when compared with normally matured DC (FIG. 3a). Thus, hCD83ext induces a reduction in DC maturation (see also increase of CD14 positive cells). In contrast, mature DC which where incubated with hCD83 for 24 hours on day 7 and analyzed on day 8, showed only a minimal influence on CD80 expression (96% to 92%), while CD83 expression was also reduced (96% to 66%) (FIG. 3b). Interestingly, CD86 expression was not influenced at any time point by the administration of hCD83ext. Also MHC class I and II expression was not affected, neither in immature nor in mature DC (Lechmann, M. et al. (2001) J. Exp. Med. 194: 1813-1821) (see FIG. 3).

Allogenic MLR:

CD4+ and CD84' T cells were isolated from buffy coats (harvested non-adherent cell fractions were incubated with neuramidase treated sheep erythrocytes, collected by ficoll gradient centrifugation and cultured in RPMI, supplemented with 5% human serum from a single AB donor) and stimulated with different ratios of mature allogenic DCs. The cells were left untreated or were incubated with different concentrations of hCD83ext or with BSA (Biorad) as a control. T-cells ($2\times10^5$/well) and DCs were co-cultivated for 4 days in 200 p,l RPMI, supplemented with 5% human serum from a single AB donor in 96-well cell culture dishes. Cells were pulsed with ($^3$H]-thymidine (1 μCi/well; Amersham Pharmacia Biotech) for 16 h. The culture supernatants were harvested onto glass fiber filtermates using an IH-110 harvester (Inotech. Dottikon, Switzerland), and filters were counted in a 1450 microplate counter (Wallac, Turku, Finnland) (Lechmann, M. et al. (2001) J. Exp. Med. 194: 1813-1821).

A typical feature of these MLR-assays is the formation of large DC-T cell-clusters. Addition of hCD83ext at day 1 strongly inhibited the typical cell cluster formation of DC and proliferating T cells (Lechmann, M. et al. (2001) J. Exp. Med. 194: 1813-1821).

Figure 4:
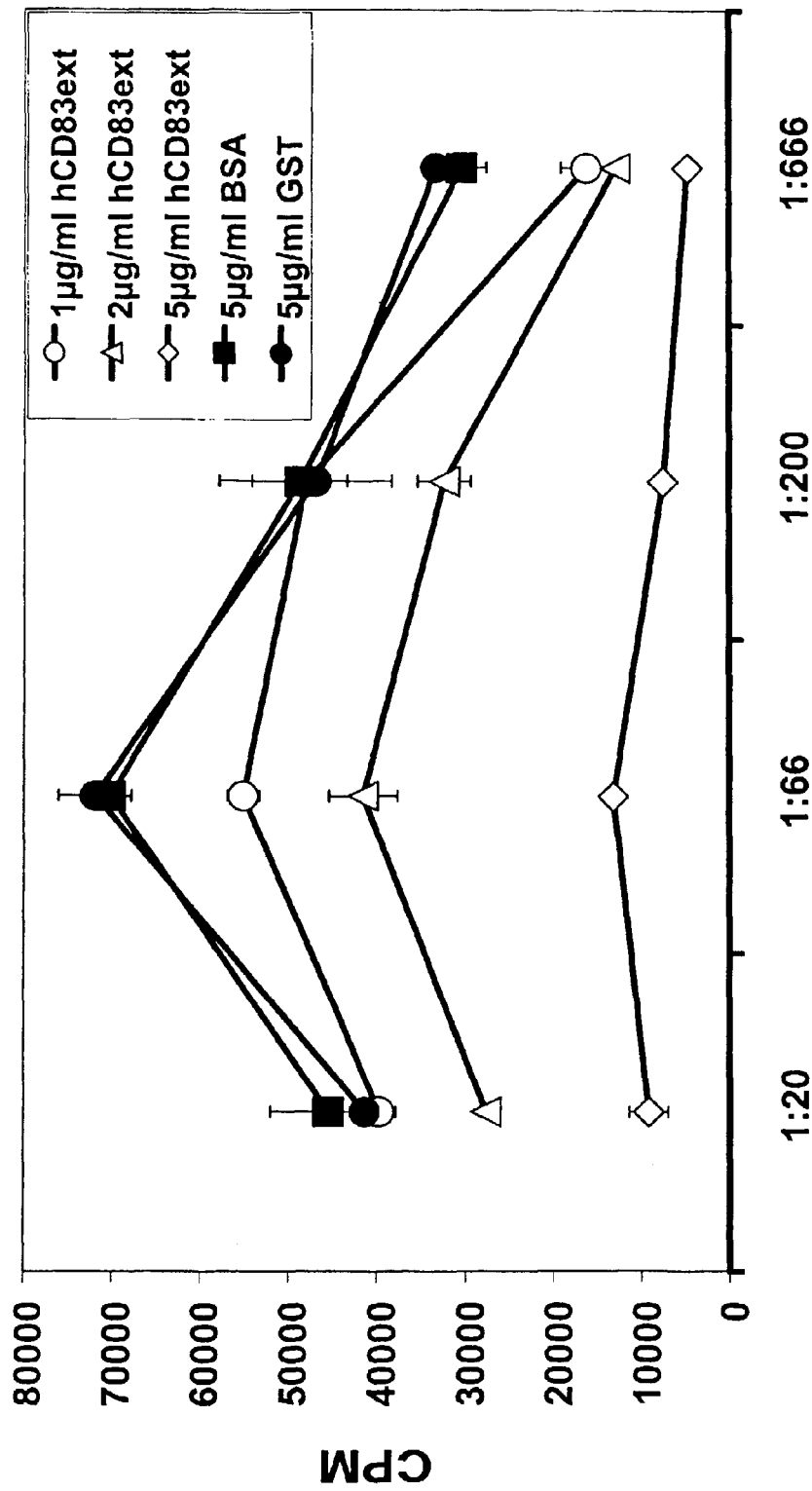
FIG. 4: hCD83ext inhibits allogeneic T cell proliferation. MLR analyses: hCD83ext reduced T cell proliferation in a dose dependent manner. GST, which was purified in the same way as hCD83ext and BSA (each 5 μg/ml) were used as controls.

Furthermore, mature dendritic cells treated with soluble hCD83ext are inhibited in a concentration dependent manner in their ability to stimulate T cell. Thus T cells do not proliferate anymore (See FIG. 4).

Example 4

In vitro Cell Cluster and MLR Experiments (Mouse)

Male or female C57/BL6 mice and BALB/C mice (Charles River, Wiga, Sulzfeld, Germany) were used at the ages of between 1 and 4 months.

Generation of Bone Marrow (BM)-DCs:

The generation of BM-DCs from C67/BL6 mice was performed exactly as described (J. Immunol. Methods 223:77, 1999). RPMI 1640 (Life Technologies, Karlsruhe, Germany) was supplemented with 100 U/ml penicillin (Sigma), 100 μg/ml streptomycin (Sigma), 2 mM L-glutamine (Sigma), 50 μg/ml ME (Sigma), 10% heat-inactivated filtered FCS (PAA, Colbe, Germany). GM-CSF was used at 200 U/ml (PrepoTech/Tebu, Rocky Hill, N.J.) on days 0, 3, 6 and 8 of incubation period.

Allogenic MLR:

CD4$^+$ and CD8$^+$ T cells were isolated from inguinal and mesentchymal lymph nodes of BALB/C mice and used for the allogenic MLR. These T-cells ($2\times20^5$ cells/well) and day 9 BM-DCs (at different ratios) were co-cultured for 3 days in 200 μl RPMI 1640 supplemented with 100 U/ml penicillin, 100 (μg/ml streptomycin, 2 mM L-glutamine, 50 μg/ml ME, 10% heat-inactivated filtered FCS in 96-well cell culture dishes. Cells were pulsed with [$^3$H]-thymidine (1μCi/well; Amersham Pharmacia Biotech) for 16 h. The culture supernatants were harvested onto glass fiber filtermates using an IH-110 harvester (Inotech, Dottikon, Switzerland), and filters were counted in a 1450 microplate counter (Wallac, Turku, Finnland).

Figure 5:
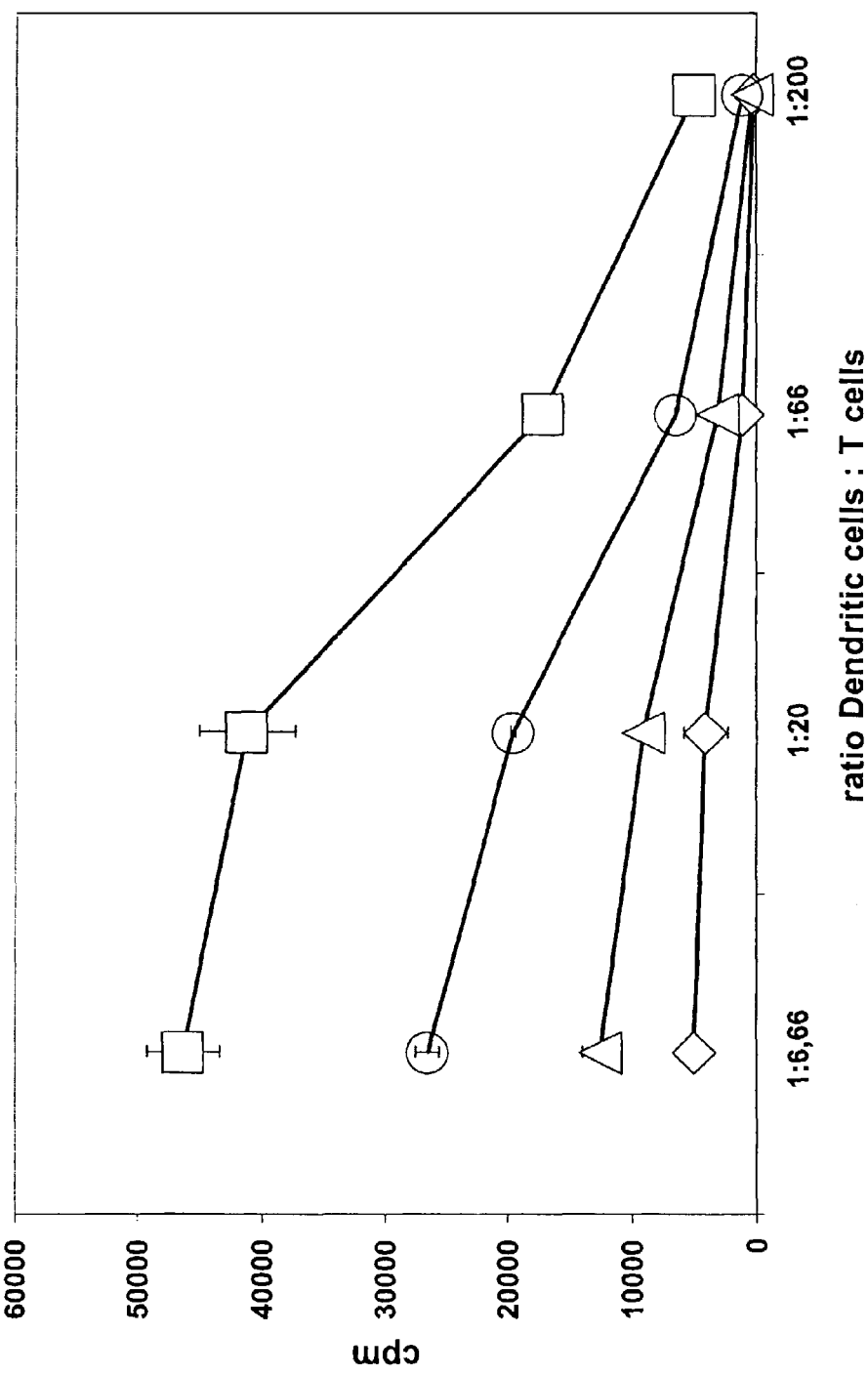
FIG. 5: hCD83ext inhibits murine allogeneic T cell proliferation. MLR analyses: hCD83ext reduced T cell proliferation in a dose dependent manner (concentration see FIG. 4). GST, which was purified in the same way as hCD83ext was used as control (5 μg/ml).

Cluster formation between mouse dendritic cells and mouse T cells was inhibited by soluble human hCD83ext. In addition, murine dendritic cells tretade with soluble human hCD83ext are inhibited in a concentration dependent manner in their ability to stimulate T cell. Thus T cells do not proliferate anymore (See FIG. 5).

Example 5

Inhibition of Experimental Autoimmune Enzephalomyelitis (EAE)

EAE is the standard model for multiple sclerosis. EAE was induced in mice by injecting subcutaneosly into both tights 50 μl of a suspension containing complete Freundsch'es adjuvans (CFA) and myelin oligodendrocyte glycoprotein ($MOG_{35-55}$) on day 0. On the same day 100 μl of pertussis toxin (2 μg/ml) were injected intraperitoneally. On day 2, a second dose of pertussis toxin was administered. Clinical signs of paralysis appeared between days 11 and 12.

To test the ability of hCD83ext to prevent and suppress paralysis associated with EAE, 100 μl hCD83 (1 μg/1 μl) were administered by injection on days—1,1 and 3 (See FIG. 6). As control, one group of mice was injected with 100 μl BSA (1 μg/1 μl). A third group of mice was left untreated. In all three groups of mice EAE was induced on day 0. Surprisingly, hCD83ext almost completely inhibited the paralysis associated with EAE.

Example 6

Production of Monoclonal Antibodies against Human CD83

Approximately 50 μg of the GST-hCD83ext fusion protein was injected intraperitoneally (ip) and subcutaneously (sc) into LOU/C rats. After a 2 months interval, a final boost with the antigen was given ip and sc 3 days before fusion. Fusion of the myeloma cell line P3X63-Ag8.653 with rat immune spleen cells was performed according to standard procedure. Hybridoma supernatants were tested in a solid-phase immunoassay using the GST-hCD83ext protein adsorbed to polystyrene microtiter plates. Following incubation with culture supernatants for 1 h, bound monoclonal antibodies were detected with peroxidase-labeled goat antirat IgG+IgM antibodies (Dianova, Hamburg, Germany) and o-phenylenediamine as chromogen in the peroxidase reaction. An irrelevant GST fusion protein served as a negative control. The immunoglobulin isotype of the monoclonal antibodies was determined using biotinylated antirat immunoglobulin (IgG) subclass-specific monoclonal antibodies (ATCC, Rockville, Md.). CD83-1G11 (rat IgG1) and CD83-4B5 (rat IgG2a) were used for Western blot and FACS analysis.

Example 7

Determination of Soluble CD83 in Patients

Using an Elisa test soluble CD83 was detected at a concentration of approx. 0.25 ng/ml (+/−0.25 ng/ml) in healthy individuals. Surprisingly, in tumor patients concentrations of up to 15 ng/ml were detected.

Thus, this test could be of diagnostic and prognostic value for tumor patients.

The invention claimed is:

1. A nucleic acid or recombinant expression vector encoding a soluble CD83 protein, said nucleic acid being a cDNA sequence, and said soluble CD83 protein being selected from the group consisting of:
   a) a protein consisting of amino acid residues 20-145 of SEQ ID NO: 2;
   b) a protein consisting of amino acid residues 1-130 of SEQ ID NO: 8;
   c) the protein of SEQ ID NO: 8; and
   d) the protein which consists of the amino acid sequence of any one of said proteins a) through c) but has one conservative amino acid substitution.

2. A prokaryotic or eukaryotic host cell transformed/transfected with a nucleic acid or a vector of claim 1.

3. A method for producing a soluble CD83 protein, which comprises culturing a transferred/transfected prokaryotic or eukaryotic host cell according to claim 2.

4. The nucleic acid or recombinant expression vector of claim 1, which encodes a CD83 protein consisting of amino acid residues −9 to 130 of SEQ ID NO: 8.

5. The nucleic acid or recombinant expression vector of claim 1, which encodes a CD83 protein consisting of the protein of SEQ ID NO: 8.

6. The nucleic acid or recombinant expression vector of claim 1, which encodes a CD83 protein consisting of the protein which consists of the amino acid sequence of any one of said proteins a) through c) but has one conservative amino acid substitution.

7. A nucleic acid or recombinant expression vector comprising a start codon operatively linked to a sequence encoding a soluble CD83 protein, said nucleic acid being a cDNA sequence, and said soluble CD83 protein being selected from the group consisting of:
   a) a protein consisting of amino acid residues 20-145 of SEQ ID NO: 2;
   b) a protein consisting of amino acid residues 1-130 of SEQ ID NO: 8;
   c) the protein of SEQ ID NO: 8;
   d) the protein which consists of the amino acid sequence of any one of said proteins a) through c) but has one conservative amino acid substitution.

* * * * *

SEQUENCE LISTING

<160> NUMBER OF SEQ ID NOS: 8

<210> SEQ ID NO 1
<211> LENGTH: 618
<212> TYPE: DNA
<213> ORGANISM: Homo sapiens
<220> FEATURE:
<221> NAME/KEY: CDS
<222> LOCATION: (1)..(615)

<400> SEQUENCE: 1

| | | | | | | | | | | | | | | | | |
|---|---|---|---|---|---|---|---|---|---|---|---|---|---|---|---|---|
| atg | tcg | cgc | ggc | ctc | cag | ctt | ctg | ctc | ctg | agc | tgc | gcc | tac | agc | ctg | 48 |
| Met | Ser | Arg | Gly | Leu | Gln | Leu | Leu | Leu | Leu | Ser | Cys | Ala | Tyr | Ser | Leu | |
| 1 | | | | 5 | | | | | 10 | | | | | 15 | | |

| gct | ccc | gcg | acg | ccg | gag | gtg | aag | gtg | gct | tgc | tcc | gaa | gat | gtg | gac | 96 |
|---|---|---|---|---|---|---|---|---|---|---|---|---|---|---|---|---|
| Ala | Pro | Ala | Thr | Pro | Glu | Val | Lys | Val | Ala | Cys | Ser | Glu | Asp | Val | Asp | |
| | | | 20 | | | | | 25 | | | | | 30 | | | |

| ttg | ccc | tgc | acc | gcc | ccc | tgg | gat | ccg | cag | gtt | ccc | tac | acg | gtc | tcc | 144 |
|---|---|---|---|---|---|---|---|---|---|---|---|---|---|---|---|---|
| Leu | Pro | Cys | Thr | Ala | Pro | Trp | Asp | Pro | Gln | Val | Pro | Tyr | Thr | Val | Ser | |
| | | | | 35 | | | | | 40 | | | | | 45 | | |

| tgg | gtc | aag | tta | ttg | gag | ggt | ggt | gaa | gag | agg | atg | gag | aca | ccc | cag | 192 |
|---|---|---|---|---|---|---|---|---|---|---|---|---|---|---|---|---|
| Trp | Val | Lys | Leu | Leu | Glu | Gly | Gly | Glu | Glu | Arg | Met | Glu | Thr | Pro | Gln | |
| | 50 | | | | | 55 | | | | | 60 | | | | | |

| gaa | gac | cac | ctc | agg | gga | cag | cac | tat | cat | cag | aag | ggg | caa | aat | ggt | 240 |
|---|---|---|---|---|---|---|---|---|---|---|---|---|---|---|---|---|
| Glu | Asp | His | Leu | Arg | Gly | Gln | His | Tyr | His | Gln | Lys | Gly | Gln | Asn | Gly | |
| 65 | | | | | 70 | | | | | 75 | | | | | 80 | |

| tct | ttc | gac | gcc | ccc | aat | gaa | agg | ccc | tat | tcc | ctg | aag | atc | cga | aac | 288 |
|---|---|---|---|---|---|---|---|---|---|---|---|---|---|---|---|---|
| Ser | Phe | Asp | Ala | Pro | Asn | Glu | Arg | Pro | Tyr | Ser | Leu | Lys | Ile | Arg | Asn | |
| | | | | 85 | | | | | 90 | | | | | 95 | | |

| act | acc | agc | tgc | aac | tcg | ggg | aca | tac | agg | tgc | act | ctg | cag | gac | ccg | 336 |
|---|---|---|---|---|---|---|---|---|---|---|---|---|---|---|---|---|
| Thr | Thr | Ser | Cys | Asn | Ser | Gly | Thr | Tyr | Arg | Cys | Thr | Leu | Gln | Asp | Pro | |
| | | | 100 | | | | | 105 | | | | | 110 | | | |

| gat | ggg | cag | aga | aac | cta | agt | ggc | aag | gtg | atc | ttg | aga | gtg | aca | gga | 384 |
|---|---|---|---|---|---|---|---|---|---|---|---|---|---|---|---|---|
| Asp | Gly | Gln | Arg | Asn | Leu | Ser | Gly | Lys | Val | Ile | Leu | Arg | Val | Thr | Gly | |
| | | | | 115 | | | | | 120 | | | | | 125 | | |

| tgc | cct | gca | cag | cgt | aaa | gaa | gag | act | ttt | aag | aaa | tac | aga | gcg | gag | 432 |
|---|---|---|---|---|---|---|---|---|---|---|---|---|---|---|---|---|
| Cys | Pro | Ala | Gln | Arg | Lys | Glu | Glu | Thr | Phe | Lys | Lys | Tyr | Arg | Ala | Glu | |
| | 130 | | | | | 135 | | | | | 140 | | | | | |

| att | gtc | ctg | ctg | ctg | gct | ctg | gtt | att | ttc | tac | tta | aca | ctc | atc | att | 480 |
|---|---|---|---|---|---|---|---|---|---|---|---|---|---|---|---|---|
| Ile | Val | Leu | Leu | Leu | Ala | Leu | Val | Ile | Phe | Tyr | Leu | Thr | Leu | Ile | Ile | |
| 145 | | | | | 150 | | | | | 155 | | | | | 160 | |

| ttc | act | tgt | aag | ttt | gca | cgg | cta | cag | agt | atc | ttc | cca | gat | ttt | tct | 528 |
|---|---|---|---|---|---|---|---|---|---|---|---|---|---|---|---|---|
| Phe | Thr | Cys | Lys | Phe | Ala | Arg | Leu | Gln | Ser | Ile | Phe | Pro | Asp | Phe | Ser | |
| | | | | 165 | | | | | 170 | | | | | 175 | | |

| aaa | gct | ggc | atg | gaa | cga | gct | ttt | ctc | cca | gtt | acc | tcc | cca | aat | aag | 576 |
|---|---|---|---|---|---|---|---|---|---|---|---|---|---|---|---|---|
| Lys | Ala | Gly | Met | Glu | Arg | Ala | Phe | Leu | Pro | Val | Thr | Ser | Pro | Asn | Lys | |
| | | | 180 | | | | | 185 | | | | | 190 | | | |

| cat | tta | ggg | cta | gtg | act | cct | cac | aag | aca | gaa | ctg | gta | tga | | | 618 |
|---|---|---|---|---|---|---|---|---|---|---|---|---|---|---|---|---|
| His | Leu | Gly | Leu | Val | Thr | Pro | His | Lys | Thr | Glu | Leu | Val | | | | |
| | | | | 195 | | | | | 200 | | | | | 205 | | |

<210> SEQ ID NO 2
<211> LENGTH: 205
<212> TYPE: PRT
<213> ORGANISM: Homo sapiens

<400> SEQUENCE: 2

Met Ser Arg Gly Leu Gln Leu Leu Leu Leu Ser Cys Ala Tyr Ser Leu
1               5                   10                  15

Ala Pro Ala Thr Pro Glu Val Lys Val Ala Cys Ser Glu Asp Val Asp
            20                  25                  30

```
Leu Pro Cys Thr Ala Pro Trp Asp Pro Gln Val Pro Tyr Thr Val Ser
        35                  40                  45

Trp Val Lys Leu Leu Glu Gly Gly Glu Glu Arg Met Glu Thr Pro Gln
 50                  55                  60

Glu Asp His Leu Arg Gly Gln His Tyr His Gln Lys Gly Gln Asn Gly
 65                  70                  75                  80

Ser Phe Asp Ala Pro Asn Glu Arg Pro Tyr Ser Leu Lys Ile Arg Asn
                 85                  90                  95

Thr Thr Ser Cys Asn Ser Gly Thr Tyr Arg Cys Thr Leu Gln Asp Pro
                100                 105                 110

Asp Gly Gln Arg Asn Leu Ser Gly Lys Val Ile Leu Arg Val Thr Gly
            115                 120                 125

Cys Pro Ala Gln Arg Lys Glu Glu Thr Phe Lys Lys Tyr Arg Ala Glu
        130                 135                 140

Ile Val Leu Leu Leu Ala Leu Val Ile Phe Tyr Leu Thr Leu Ile Ile
145                 150                 155                 160

Phe Thr Cys Lys Phe Ala Arg Leu Gln Ser Ile Phe Pro Asp Phe Ser
                165                 170                 175

Lys Ala Gly Met Glu Arg Ala Phe Leu Pro Val Thr Ser Pro Asn Lys
            180                 185                 190

His Leu Gly Leu Val Thr Pro His Lys Thr Glu Leu Val
        195                 200                 205

<210> SEQ ID NO 3
<211> LENGTH: 2051
<212> TYPE: DNA
<213> ORGANISM: Mus musculus
<220> FEATURE:
<221> NAME/KEY: CDS
<222> LOCATION: (14)..(601)

<400> SEQUENCE: 3
gcgctccagc cgc atg tcg caa ggc ctc cag ctc ctg ttt cta ggc tgc     49
            Met Ser Gln Gly Leu Gln Leu Leu Phe Leu Gly Cys
              1               5                  10 gcc tgc agc ctg gca ccc gcg atg gcg atg cgg gag gtg acg gtg gct    97
Ala Cys Ser Leu Ala Pro Ala Met Ala Met Arg Glu Val Thr Val Ala
         15                  20                  25 tgc tcc gag acc gcc gac ttg cct tgc aca gcg ccc tgg gac ccg cag    145
Cys Ser Glu Thr Ala Asp Leu Pro Cys Thr Ala Pro Trp Asp Pro Gln
 30                  35                  40 ctc tcc tat gca gtg tcc tgg gcc aag gtc tcc gag agt ggc act gag    193
Leu Ser Tyr Ala Val Ser Trp Ala Lys Val Ser Glu Ser Gly Thr Glu
 45                  50                  55                  60 agt gtg gag ctc ccg gag agc aag caa aac agc tcc ttc gag gcc ccc    241
Ser Val Glu Leu Pro Glu Ser Lys Gln Asn Ser Ser Phe Glu Ala Pro
                 65                  70                  75 agg aga agg gcc tat tcc ctg acg atc caa aac act acc atc tgc agc    289
Arg Arg Arg Ala Tyr Ser Leu Thr Ile Gln Asn Thr Thr Ile Cys Ser
             80                  85                  90 tcg ggc acc tac agg tgt gcc ctg cag gag ctc gga ggg cag cgc aac    337
Ser Gly Thr Tyr Arg Cys Ala Leu Gln Glu Leu Gly Gly Gln Arg Asn
         95                 100                 105 ttg agc ggc acc gtg gtt ctg aag gtg aca gga tgc ccc aag gaa gct    385
Leu Ser Gly Thr Val Val Leu Lys Val Thr Gly Cys Pro Lys Glu Ala
110                 115                 120 aca gag tca act ttc agg aag tac agg gca gaa gct gtg ttg ctc ttc    433
Thr Glu Ser Thr Phe Arg Lys Tyr Arg Ala Glu Ala Val Leu Leu Phe
125                 130                 135                 140
```

-continued

```
tct ctg gtt gtt ttc tac ctg aca ctc atc att ttc acc tgc aaa ttt     481
Ser Leu Val Val Phe Tyr Leu Thr Leu Ile Ile Phe Thr Cys Lys Phe
            145                 150                 155 gca cga cta caa agc att ttc cca gat att tct aaa cct ggt acg gaa     529
Ala Arg Leu Gln Ser Ile Phe Pro Asp Ile Ser Lys Pro Gly Thr Glu
        160                 165                 170 caa gct ttt ctt cca gtc acc tcc cca agc aaa cat ttg ggg cca gtg     577
Gln Ala Phe Leu Pro Val Thr Ser Pro Ser Lys His Leu Gly Pro Val
    175                 180                 185 acc ctt cct aag aca gaa acg gta tgagtaggat ctccactggt ttttacaaag    631
Thr Leu Pro Lys Thr Glu Thr Val
    190                 195 ccaagggcac atcagatcag tgtgcctgaa tgccacccgg acaagagaag aatgagctcc    691
atcctcagat ggcaaccttt ctttgaagtc cttcacctga cagtgggctc cacactactc    751
cctgacacag ggtcttgagc accatcatat gatcacgaag catggagtat caccgcttct    811
ctgtggctgt cagcttaatg tttcatgtgg ctatctggtc aacctcgtga gtgcttttca    871
gtcatctaca agctatggtg agatgcaggt gaagcagggt catgggaaat ttgaacactc    931
tgagctggcc ctgtgacaga ctcctgagga cagctgtcct ctcctacatc tgggatacat    991
ctctttgaat ttgtcctgtt tcgttgcacc agcccagatg tctcacatct ggcggaaatt   1051
gacaggccaa gctgtgagcc agtgggaaat atttagcaaa taatttccca gtgcgaaggt   1111
cctgctatta gtaaggagta ttatgtgtac atagaaatga gaggtcagtg aactattccc   1171
cagcagggcc ttttcatctg gaaaagacat ccacaaaagc agcaatacag agggatgcca   1231
catttatttt tttaatcttc atgtacttgt caaagaagaa ttttttcatgt ttttttcaaag   1291 aagtgtgttt ctttccttt ttaaaatatg aaggtctagt tacatagcat tgctagctga   1351
caagcagcct gagagaagat ggagaatgtt cctcaaaata gggacagcaa gctagaagca   1411
ctgtacagtg ccctgctggg aagggcgaga catggactga gaaccagaa gtctggccac   1471 aagattgtct gtatgattct ggacgagtca cttgtggttt tcactctctg ttagtaaac   1531 cagatagttt agtctgggtt gaatacaatg gatgtgaagt tgcttgggga agctgaatg   1591 tagtgaatac attggcaact ctactgggct gttaccttgt tgatatccta gagttctgga   1651
gctgagcgaa tgcctgtcat atctcagctt gcccatcaat ccaaacacag gaggctacaa   1711
aaaggacatg agcatggtct tctgtgtgaa ctcctcctga aaacgtgga gactggctca   1771 gcgctttgcg cttgaaggac taatcacaag ttcttgaaga tatggaccta ggggagctat   1831
tgcgccacga caggaggaag ttctcagatg ttgcattgat gtaacattgt tgcatttctt   1891
taatgagctg ggctccttcc tcatttgctt cccaaagaga ttttgtccca ctaatggtgt   1951
gcccatcacc cacactatga aagtaaaagg gatgctgagc agatacagcg tgcttacctc   2011
tcagccatga ctttcatgct attaaaagaa tgcatgtgaa                        2051
```

<210> SEQ ID NO 4
<211> LENGTH: 196
<212> TYPE: PRT
<213> ORGANISM: Mus musculus

<400> SEQUENCE: 4

Met Ser Gln Gly Leu Gln Leu Leu Phe Leu Gly Cys Ala Cys Ser Leu
 1               5                  10                  15

Ala Pro Ala Met Ala Met Arg Glu Val Thr Val Ala Cys Ser Glu Thr
            20                  25                  30

```
Ala Asp Leu Pro Cys Thr Ala Pro Trp Asp Pro Gln Leu Ser Tyr Ala
            35                  40                  45

Val Ser Trp Ala Lys Val Ser Glu Ser Gly Thr Glu Ser Val Glu Leu
 50                  55                  60

Pro Glu Ser Lys Gln Asn Ser Ser Phe Glu Ala Pro Arg Arg Arg Ala
 65                  70                  75                  80

Tyr Ser Leu Thr Ile Gln Asn Thr Thr Ile Cys Ser Ser Gly Thr Tyr
                85                  90                  95

Arg Cys Ala Leu Gln Glu Leu Gly Gly Gln Arg Asn Leu Ser Gly Thr
            100                 105                 110

Val Val Leu Lys Val Thr Gly Cys Pro Lys Glu Ala Thr Glu Ser Thr
            115                 120                 125

Phe Arg Lys Tyr Arg Ala Glu Ala Val Leu Leu Phe Ser Leu Val Val
130                 135                 140

Phe Tyr Leu Thr Leu Ile Ile Phe Thr Cys Lys Phe Ala Arg Leu Gln
145                 150                 155                 160

Ser Ile Phe Pro Asp Ile Ser Lys Pro Gly Thr Glu Gln Ala Phe Leu
                165                 170                 175

Pro Val Thr Ser Pro Ser Lys His Leu Gly Pro Val Thr Leu Pro Lys
            180                 185                 190

Thr Glu Thr Val
        195

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: primer for
      the extracellular domain of CD83

<400> SEQUENCE: 5
tcccccggga acgccggagg tgaaggtggc t                                      31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: primer for
      the extracellular domain of CD83

<400> SEQUENCE: 6
aattagaatt ctcaaatctc cgctctgtat t                                      31

<210> SEQ ID NO 7
<211> LENGTH: 435
<212> TYPE: DNA
<213> ORGANISM: Artificial Sequence
<220> FEATURE:
<221> NAME/KEY: CDS
<222> LOCATION: (1)..(417)
<220> FEATURE:
<221> NAME/KEY: mat_peptide
<222> LOCATION: (28)..(417)
<223> OTHER INFORMATION: A polynucleotide sequence encoding a soluble
      form of the CD83 protein.

<400> SEQUENCE: 7 cct cca aaa tcg gat ctg gtt ccg cgt gga tcc ccg gga acg ccg gag       48
Pro Pro Lys Ser Asp Leu Val Pro Arg Gly Ser Pro Gly Thr Pro Glu
            -5                  -1   1                   5
```

```
gtg aag gtg gct tgc tcc gaa gat gtg gac ttg ccc tgc acc gcc ccc     96
Val Lys Val Ala Cys Ser Glu Asp Val Asp Leu Pro Cys Thr Ala Pro
        10                  15                  20 tgg gat ccg cag gtt ccc tac acg gtc tcc tgg gtc aag tta ttg gag    144
Trp Asp Pro Gln Val Pro Tyr Thr Val Ser Trp Val Lys Leu Leu Glu
    25                  30                  35 ggt ggt gaa gag agg atg gag aca ccc cag gaa gac cac ctc agg gga    192
Gly Gly Glu Glu Arg Met Glu Thr Pro Gln Glu Asp His Leu Arg Gly
40                  45                  50                  55 cag cac tat cat cag aag ggg caa aat ggt tct ttc gac gcc ccc aat    240
Gln His Tyr His Gln Lys Gly Gln Asn Gly Ser Phe Asp Ala Pro Asn
                60                  65                  70 gaa agg ccc tat tcc ctg aag atc cga aac act acc agc tgc aac tcg    288
Glu Arg Pro Tyr Ser Leu Lys Ile Arg Asn Thr Thr Ser Cys Asn Ser
            75                  80                  85 ggg aca tac agg tgc act ctg cag gac ccg gat ggg cag aga aac cta    336
Gly Thr Tyr Arg Cys Thr Leu Gln Asp Pro Asp Gly Gln Arg Asn Leu
        90                  95                 100 agt ggc aag gtg atc ttg aga gtg aca gga tgc cct gca cag cgt aaa    384
Ser Gly Lys Val Ile Leu Arg Val Thr Gly Cys Pro Ala Gln Arg Lys
    105                 110                 115 gaa gag act ttt aag aaa tac aga gcg gag att tgagaattca tcgtgact    435
Glu Glu Thr Phe Lys Lys Tyr Arg Ala Glu Ile
120                 125                 130

<210> SEQ ID NO 8
<211> LENGTH: 139
<212> TYPE: PRT
<213> ORGANISM: Artificial Sequence
<220> FEATURE:
<223> OTHER INFORMATION: The sequence of amino acids comprising a
      soluble form of the CD83 protein.

<400> SEQUENCE: 8

Pro Pro Lys Ser Asp Leu Val Pro Arg Gly Ser Pro Gly Thr Pro Glu
                -5                  -1  1               5

Val Lys Val Ala Cys Ser Glu Asp Val Asp Leu Pro Cys Thr Ala Pro
        10                  15                  20

Trp Asp Pro Gln Val Pro Tyr Thr Val Ser Trp Val Lys Leu Leu Glu
    25                  30                  35

Gly Gly Glu Glu Arg Met Glu Thr Pro Gln Glu Asp His Leu Arg Gly
40                  45                  50                  55

Gln His Tyr His Gln Lys Gly Gln Asn Gly Ser Phe Asp Ala Pro Asn
                60                  65                  70

Glu Arg Pro Tyr Ser Leu Lys Ile Arg Asn Thr Thr Ser Cys Asn Ser
            75                  80                  85

Gly Thr Tyr Arg Cys Thr Leu Gln Asp Pro Asp Gly Gln Arg Asn Leu
        90                  95                 100

Ser Gly Lys Val Ile Leu Arg Val Thr Gly Cys Pro Ala Gln Arg Lys
    105                 110                 115

Glu Glu Thr Phe Lys Lys Tyr Arg Ala Glu Ile
120                 125                 130
```